United States Patent
Froissant et al.

(10) Patent No.: US 7,547,706 B2
(45) Date of Patent: Jun. 16, 2009

(54) 1H-PYRIMIDO[4,5-B]INDOLE DERIVATIVES, THEIR PREPARATION AND THERAPEUTIC USE

(75) Inventors: Jacques Froissant, Brevainville (FR); Frank Marguet, Verrieres le Buisson (FR); Anne Olivier-Bandini, Paris (FR); Frederic Puech, Gif sur Yvette (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/873,789

(22) Filed: Oct. 17, 2007

(65) Prior Publication Data
US 2008/0125410 A1     May 29, 2008

Related U.S. Application Data

(63) Continuation of application No. PCT/FR2006/000843, filed on Apr. 18, 2006.

(30) Foreign Application Priority Data
Apr. 20, 2005 (FR) .................................. 05 03934

(51) Int. Cl.
A01N 43/54      (2006.01)
A61K 31/505    (2006.01)
C07D 239/00   (2006.01)
C07D 471/00   (2006.01)
C07D 487/00   (2006.01)
C07D 491/00   (2006.01)

(52) U.S. Cl. ....................................... 514/267; 544/250
(58) Field of Classification Search ................ 514/267; 544/250

See application file for complete search history.

(56) References Cited

FOREIGN PATENT DOCUMENTS

WO     WO 93/20078     10/1993
WO     96/26941     * 9/1996
WO     WO 96/26941      9/1996

OTHER PUBLICATIONS

Bundy, G. L., et. al., Synthesis of 2,4-Di-1-Pyrrolidinyl-9H-Pyrimido[4,5-b]Indoles, Including Antiasthma Clinical Candidate PNU-142731A, ORganic Process Research and Development, (2001), vol. 5, pp. 144-151.

Bundy, G. L., et. al., Synthesis of Novel 2,4-Diaminopyrrolo[2,3-d]Pyrimidines with Antioxidant, Neuroprotective, and Antiasthma Activity, J. Med. Chem. (1995) vol. 38, pp. 4161-4163.

Dotzauer, B., et. al., Synthesis of Medicinally Interesting 2, 4-Diamino-9H-Pyrimido[4,5-b]Indol-6-ols via Extension of the Nenitzescu Reaction, Synlett, (2004), vol. 6, pp. 1039-1043.

Kondo, Y., et. al., Condensed Heteroaromatic Ring Systems. XVI. Synthesis of Pyrrolo[2,3-d]Pyrimidine Derivatives, Database CA, Database accession No. 1990:459080, Chemical & Pharmaceutical Bulletin, vol. 37, No. 11, 2933-6 (1989).

* cited by examiner

*Primary Examiner*—James O Wilson
*Assistant Examiner*—Erich A Leeser
(74) *Attorney, Agent, or Firm*—Balaram Gupta; Kelly L. Bender

(57) ABSTRACT

The invention concerns compounds of general formula (I):

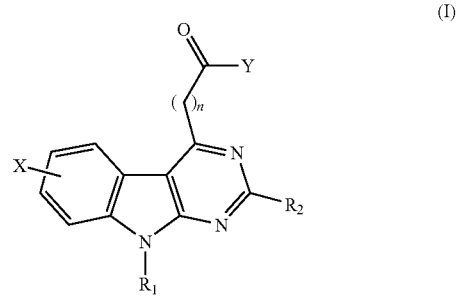

Wherein n, X, Y, $R_1$ and $R_2$ are as defined herein. The invention also concerns a method for preparing the compounds and their therapeutic use.

13 Claims, No Drawings

1H-PYRIMIDO[4,5-B]INDOLE DERIVATIVES, THEIR PREPARATION AND THERAPEUTIC USE

This application is a continuation of International application No. PCT/FR2006/000,843, filed Apr. 18, 2006, which is incorporated herein by reference in its entirety; which claims the benefit of priority of French Patent Application No. 05/03,934, filed Apr. 20, 2005.

One subject of the invention is 1H-pyrimido[4,5-b]indole derivatives.

A first subject of the invention relates to the compounds corresponding to the general formula (I) below.

Another subject of the invention relates to processes for preparing compounds of general formula (I).

Another subject of the invention relates to compounds that can be used, in particular, as intermediates for synthesizing compounds of general formula (I).

Another subject of the invention relates to the uses of compounds of general formula (I), especially in medications or in pharmaceutical compositions.

The compounds of the invention correspond to the general formula (I):

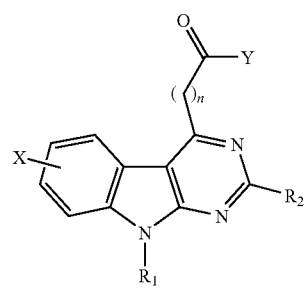

in which:
n represents the number 0 or 1;
X represents a hydrogen or halogen atom;
Y represents an $OR_3$ group or an $NR_4R_5$ group;
$R_1$ represents a hydrogen atom or a ($C_1$-$C_6$)alkyl group;
$R_2$ represents a ($C_1$-$C_6$)alkyl group, a phenyl or a monocyclic or bicyclic heterocycle, said phenyl or heterocycle groups possibly bearing one or more halogen atoms and/or one or more ($C_1$-$C_6$)alkyl, ($C_1$-$C_6$)alkoxyl, ($C_1$-$C_6$)alkoxy ($C_1$-$C_6$)alkyl, ($C_1$-$C_6$)alkylamino ($C_1$-$C_6$)alkyl or ($C_1$-$C_6$)dialkylamino ($C_1$-$C_6$)alkyl groups;
$R_3$ represents a hydrogen atom, a ($C_1$-$C_6$)alkyl group or a benzyl; and
$R_4$ and $R_5$ each represent, independently of one another, a hydrogen atom or a ($C_1$-$C_6$)alkyl group, or else $R_4$ and $R_5$ form, with the nitrogen atom that they bear, an aziridinyl, azetidinyl, pyrrolidinyl, piperidinyl, morpholinyl, thiomorpholinyl or piperazinyl, optionally substituted by a ($C_1$-$C_6$)alkyl, phenyl or heterocycle.

The compounds of formula (I) may comprise one or more asymmetric carbon atoms. They may therefore exist in the form of enantiomers or of diastereoisomers. These enantiomers, diastereoisomers and also mixtures thereof, including racemic mixtures, form part of the invention.

The compounds of formula (I) may exist in the base or acid addition salt form. Such addition salts form part of the invention. These salts are advantageously prepared with pharmaceutically acceptable acids, but the salts of other acids that are useful, for example, for purifying or isolating compounds of formula (I) also form part of the invention.

The compounds of formula (I) may also exist in the form of hydrates or solvates, namely in the form of associations or combinations with one or more water molecules or with a solvent. Such hydrates and solvates also form part of the invention.

Within the scope of the present invention:
a halogen atom represents a fluorine, a chlorine, a bromine or an iodine atom;
($C_t$-$C_z$) where t and z may take the values of 1 to 6, represents a carbon-based chain which may have from 1 to 6 carbon atoms;
an alkyl group represents a saturated, linear, branched or cyclic or combination thereof, aliphatic group optionally substituted by one or more halogen atoms. As examples, mention may be made of methyl, ethyl, propyl, isopropyl, butyl, isobutyl, tert-butyl, pentyl, cyclopropyl, methylcyclopropyl, cyclopropylmethyl, cyclobutyl, cyclopentyl, cyclohexyl, fluoromethyl or trifluoromethyl groups;
an alkoxyl group represents an oxygen atom substituted by an alkyl group where the alkyl group is as defined previously. By way of example, mention may be made of the methoxyl group;
an alkylamino group represents an amine substituted by an alkyl group where the alkyl group is as defined previously. By way of example, mention may be made of the methylamino group;
an alkylaminoalkyl group represents an alkyl group substituted by an alkylamino group. By way of example, mention may be made of the (methylamino)methyl group;
a dialkylamino group represents an amine substituted by two alkyl groups, where each alkyl group is as defined previously. By way of example, mention may be made of the dimethylamino group;
a dialkylaminoalkyl group represents an alkyl group substituted by a dialkylamino group. By way of example, mention may be made of the (dimethylamino)methyl group;
an alkoxyalkyl group represents an alkyl group substituted by an alkoxyl group. By way of examples, mention may be made of the methoxymethyl, ethoxymethyl or methoxyethyl groups; and
a heterocycle represents a saturated, partially saturated or aromatic ring with 4 to 12 chain members having at least one atom chosen from O, S or N. As examples of monocyclic heterocycles, mention may be made of pyridinyl, pyrimidinyl, pyrazinyl, pyridazinyl, thiazolyl, furanyl, thiophenyl or tetrahydropyranyl groups. As examples of bicyclic heterocycles, mention may be made of the quinolinyl, dihydroquinolinyl, tetrahydroquinolinyl, isoquinolinyl, quinoxalinyl, quinoazolinyl, phthalazinyl, cinnolinyl, benzothiazolyl, benzofuranyl or benzothiophenyl groups.

A first subgroup of compounds of general formula (I) is composed of compounds for which:
n represents the number 0 or 1;
X represents a hydrogen or halogen atom;
Y represents an $OR_3$ group or an $NR_4R_5$ group;
$R_1$ represents a hydrogen atom or a ($C_1$-$C_6$)alkyl group;
$R_2$ represents a phenyl or a heterocycle of pyridinyl, pyrimidinyl, pyrazinyl or pyridazinyl type, the phenyl or the heterocycle possibly bearing one or more halogen atoms and/or one or more ($C_1$-$C_6$)alkyl or ($C_1$-$C_6$)alkoxyl groups;
$R_3$ represents a hydrogen, a ($C_1$-$C_6$)alkyl or a benzyl; and R$_4$ and R$_5$ each represent, each independently of one another, a hydrogen atom or a (C$_1$-C$_6$)alkyl group, or else R$_4$ and R$_5$ form, with the nitrogen atom that they bear, an aziridinyl, azetidinyl, pyrrolidinyl, piperidinyl, morpholinyl, thiomorpholinyl or piperazinyl group, optionally substituted by a (C$_1$-C$_6$)alkyl, phenyl or azetidinyl.

A second subgroup of compounds of general formula (I) is composed of compounds for which:

n represents the number 0 or 1; and/or

X represents a hydrogen or halogen atom, more particularly a chlorine or fluorine; and/or Y represents an OR$_3$ group or an NR$_4$R$_5$ group; and/or R$_1$ represents a hydrogen atom or a (C$_1$-C$_6$)alkyl group, more particularly a methyl; and/or R$_2$ represents a phenyl or a heterocycle of pyridinyl or pyrazinyl type, the phenyl or the heterocycle possibly bearing one or more (C$_1$-C$_6$)alkyl groups, more particularly methyl, or (C$_1$-C$_6$)alkoxyl groups, more particularly methoxy; and/or R$_3$ represents a hydrogen or a (C$_1$-C$_6$)alkyl, more particularly a methyl or an ethyl; and/or R$_4$ and R$_5$ each represent, each independently of one another, a (C$_1$-C$_6$)alkyl group, more particularly a methyl or an ethyl, or else R$_4$ and R$_5$ form, with the nitrogen atom that they bear, a pyrrolidinyl, piperidinyl, morpholinyl or piperazinyl group, optionally substituted by a (C$_1$-C$_6$)alkyl, more particularly methyl, or an azetidinyl.

A third subgroup of compounds of general formula (I) is composed of the compounds for which:

n represents the number 0 or 1;

X represents a hydrogen or fluorine or chlorine atom;

Y represents a hydroxy, OCH$_3$, O(CH$_2$CH$_3$), N(CH$_3$)$_2$, N(CH$_2$CH$_3$)$_2$, pyrrolidinyl, piperidinyl, morpholinyl, (N-azetidinyl)piperidinyl or N-methylpiperazinyl group;

R$_1$ represents a hydrogen atom, a methyl or isobutyl group; and

R$_2$ represents a phenyl, a methyl, isopropyl or cyclopropyl group or a heterocycle of pyridinyl, pyrazinyl, pyrimidinyl, thiazolyl, tetrahydroquinolinyl or tetrahydropyranyl type, the phenyl and heterocycle groups possibly optionally being substituted by one or more halogen groups and/or one or more (C$_1$-C$_6$)alkyl, (C$_1$-C$_6$)alkoxyl, (C$_1$-C$_6$)alkoxy (C$_1$-C$_6$)alkyl, (C$_1$-C$_6$)dialkylamino, (C$_1$-C$_6$)dialkylamino (C$_1$-C$_6$)alkyl groups.

Among the compounds of formula (I) that are subjects of the invention, mention may especially be made of the following compounds:

1. N,N,9-trimethyl-2-phenyl-9H-pyrimido[4,5-b]indole-4-carboxamide;
2. 7-chloro-N,N,9-trimethyl-2-phenyl-9H-pyrimido[4,5-b]indole-4-carboxamide;
3. 7-fluoro-N,N-9-trimethyl-2-phenyl-9H-pyrimido[4,5-b]indole-4-carboxamide;
4. 6-chloro-N,N-9-trimethyl-2-phenyl-9H-pyrimido[4,5-b]indole-4-carboxamide;
5. 7-chloro-N,N-dimethyl-2-phenyl-9H-pyrimido[4,5-b]indole-4-carboxamide;
6. 7-chloro-N,N-diethyl-9-methyl-2-phenyl-9H-pyrimido[4,5-b]indole-4-carboxamide;
7. 7-chloro-9-methyl-2-phenyl-4-(pyrrolidin-1-ylcarbonyl)-9H-pyrimido[4,5-b]indole;
8. 7-chloro-9-methyl-2-phenyl-4-(piperidin-1-ylcarbonyl)-9H-pyrimido[4,5-b]indole;
9. 7-chloro-9-methyl-4-(morpholin-4-ylcarbonyl)-2-phenyl-9H-pyrimido[4,5-b]indole;
10. 4-[(4-azetidin-1-yl)piperidin-1-ylcarbonyl]-7-chloro-9-methyl-2-phenyl-9H-pyrimido-[4,5-b]indole;
11. 7-chloro-9-methyl-4-[(4-methylpiperazin-1-yl)carbonyl]-2-phenyl-9H-pyrimido[4,5-b]indole;
12. 6-chloro-N,N-9-trimethyl-2-pyridin-4-yl-9H-pyrimido[4,5-b]indole-4-carboxamide;
13. 7-fluoro-N,N,9-trimethyl-2-pyridin-4-yl-9H-pyrimidol[4,5-b]indole-4-carboxamide;
14. 7-chloro-9-methyl-2-pyridin-4-yl-4-(pyrrolidin-1-ylcarbonyl)-9H-pyrimido-[4,5-b]indole;
15. 7-chloro-N,N,9-trimethyl-2-pyridin-4-yl-9H-pyrimido[4,5-b]indole-4-carboxamide;
16. 7-chloro-N,N,9-trimethyl-2-pyridin-3-yl-9H-pyrimido[4,5-b]indole-4-carboxamide;
17. 7-chloro-N,N-9-trimethyl-2-pyridin-2-yl-9H-pyrimido[4,5-b]indole-4-carboxamide
18. 7-chloro-N,N-9-trimethyl-2-pyrazin-2-yl-9H-pyrimido[4,5-b]indole-4-carboxamide;
19. 2-(7-chloro-9-methyl-2-phenyl-9H-pyrimido[4,5-b]indol-4-yl)-N,N-dimethylacetamide;
20. 2-(6-chloro-9-methyl-2-phenyl-9H-pyrimido[4,5-b]indol-4-yl)-N,N-dimethylacetamide;
21. 2-(7-chloro-9-methyl-2-pyridin-4-yl-9H-pyrimido[4,5-b]indol-4-yl)-N,N-dimethylacetamide;
22. 2-(7-chloro-9-methyl-2-pyridin-3-yl-9H-pyrimido[4,5-b]indol-4-yl)-N,N-dimethylacetamide;
23. N,N-dimethyl-2-phenyl-9H-pyrimido[4,5-b]indole-4-carboxamide;
24. ethyl 7-chloro-9-methyl-2-phenyl-9H-pyrimido[4,5-b]indole-4-carboxylate;
25. methyl 7-chloro-9-methyl-2-phenyl-9H-pyrimido[4,5-b]indole-4-carboxylate;
26. 7-chloro-9-methyl-2-phenyl-9H-pyrimido[4,5-b]indole-4-carboxylic acid;
27. 7-chloro-N,N-9-trimethyl-2-(6-methylpyridin-3-yl)-9H-pyrimido[4,5-b]indole-4-carboxamide;
28. 7-chloro-2-(6-methoxypyridin-3-yl)-N,N,9-trimethyl-9H-pyrimido[4,5-b]indole-4-carboxamide;
29. 7-chloro-N,N-9-trimethyl-2-(2-methylpyridin-4-yl)-9H-pyrimido[4,5-b]indole-4-carboxamide;
30. 7-chloro-2-(2-methoxypyridin-4-yl)-N,N,9-trimethyl-9H-pyrimido[4,5-b]indole-4-carboxamide;
31. 7-chloro-9-isobutyl-N,N-dimethyl-2-pyridin-4-yl-9H-pyrimido[4,5-b]indole-4-carboxamide;
32. 7-chloro-2-cyclopropyl-N,N,9-trimethyl-9H-pyrimido[4,5-b]indole-4-carboxamide;
33. 7-chloro-N,N,2,9-tetramethyl-9H-pyrimido[4,5-b]indole-4-carboxamide;
34. 7-chloro-2-isopropyl-N,N,9-trimethyl-9H-pyrimido[4,5-b]indole-4-carboxamide;
35. 7-chloro-N,N,9-trimethyl-2-(tetrahydro-2H-pyran-4-yl)-9H-pyrimido[4,5-b]indole-4-carboxamide;
36. 7-chloro-2-{4-[(dimethylamino)methyl]phenyl-N,N,9-trimethyl-9H-pyrimido[4,5-b]indole-4-carboxamide;
37. 7-chloro-2-(6-chloropyridin-3-yl)-N,N,9-trimethyl-9H-pyrimido[4,5-b]indole-4-carboxamide;
38. 7-chloro-N,N,9-trimethyl-2-[6-trifluoromethyl)pyridin-3-yl]-9H-pyrimido[4,5-b]indole-4-carboxamide;
39. 7-chloro-2-(6-ethoxypyridin-3-yl)-N,N,9-trimethyl-9H-pyrimido[4,5-b]indole-4-carboxamide;
40. 7-chloro-2-(6-ethylpyridin-3-yl)-N,N,9-trimethyl-9H-pyrimido[4,5-b]indole-4-carboxamide;
41. 7-chloro-2-(5-ethylpyridin-3-yl)-N,N,9-trimethyl-9H-pyrimido[4,5-b]indole-4-carboxamide;
42. 7-chloro-N,N,9-trimethyl-2-(5-methylpyridin-3-yl)-9H-pyrimido[4,5-b]indole-4-carboxamide;
43. 7-chloro-N,N,9-trimethyl-2-pyrimidin-5-yl-9H-pyrimido[4,5-b]indole-4-carboxamide;
44. 7-chloro-2-(5-methoxypyridin-3-yl)-N,N,9-trimethyl-9H-pyrimido[4,5-b]indole-4-carboxamide;
45. 7-chloro-2-[6-(methoxymethyl)pyridin-3-yl]-N,N,9-trimethyl-9H-pyrimido[4,5-b]indole-4-carboxamide;
46. 7-chloro-N,N,9-trimethyl-2-(2-methyl-1,3-thiazol-4-yl)-9H-pyrimido[4,5-b]indole-4-carboxamide;

47. 7-chloro-2-{6-[(dimethylamino)methyl]pyridin-3-yl}-N,N,9-trimethyl-9H-pyrimido[4,5-b]indole-4-carboxamide;
48. 7-chloro-2-(5,6-dimethylpyridin-3-yl)-N,N,9-trimethyl-9H-pyrimido[4,5-b]indole-4-carboxamide;
49. 7-chloro-N,N,9-trimethyl-2-(5,6,7,8-tetrahydroquinolin-3-yl)9H-pyrimido[4,5-b]indole-4-carboxamide;
50. 7-chloro-2-(2,6-dimethylpyridin-4-yl)-N,N,9-trimethyl-9H-pyrimido[4,5-b]indole-4-carboxamide.

The compounds of general formula (I) may be prepared by the processes illustrated by the following schemes.

The expression "leaving group" is understood to mean, in that which follows, a group which may be easily split from a molecule by cleavage of a heterolytic bond with departure of an electron pair. This group can thus be easily replaced by another group during a substitution reaction, for example. Such leaving groups are, for example, halogens or an activated hydroxy group such as a mesyl, tosyl, triflate, acetyl, etc. Examples of leaving groups and also references for their preparation are given in "Advances in Organic Chemistry", J. March, 3rd edition, Wiley Interscience, p. 310-316.

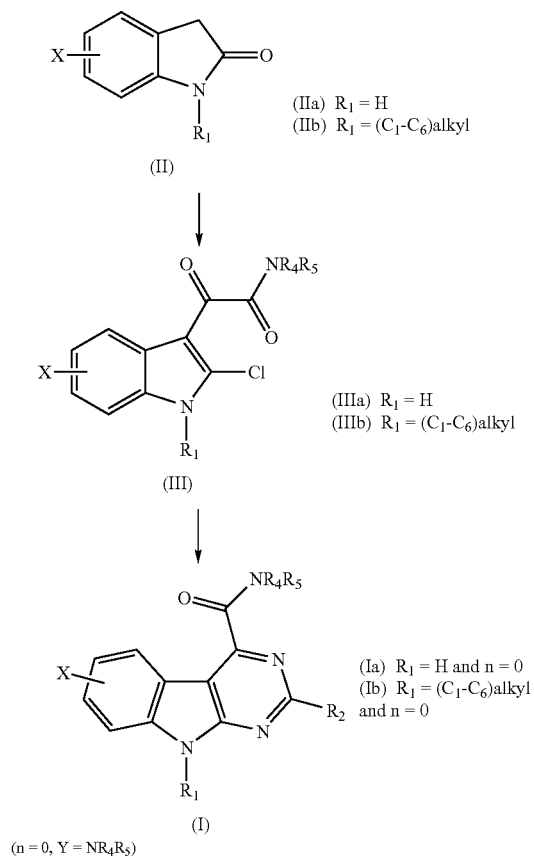

Synthetic Pathway for Carboxamides (n=0, Y=NR$_4$R$_5$)

As illustrated in scheme 1, a 2-oxindole of general formula (II), in which X and R$_1$ are as defined above, is converted to 2-chloroindole of general formula (III), in which X, R$_1$, R$_4$ and R$_5$ are as defined above, first by action of oxalyl chloride in a polar aprotic solvent such as dichloromethane for example, then by action of an amine of general formula HNR$_4$R$_5$, in which R$_4$ and R$_5$ are as defined above. The 2-chloroindole of general formula (III) is cyclized in the presence of an alkyl, heteroalkyl, aryl or heteroaryl amidine of general formula R$_2$C(NH)NH$_2$ in which R$_2$ is as defined above, by heating in an apolar or polar solvent such as for example xylene or N,N-dimethylformamide in order to result in a compound of general formula (I) in which X, R$_1$, R$_2$, R$_4$ and R$_5$ are as defined above.

The compounds (Ib) for which R$_1$=(C$_1$-C$_6$)alkyl may be obtained from compounds (Ia) for which R$_1$=H via an alkylation reaction, for example using 1,1-di(C$_1$-C$_6$)alkoxytrimethylamine in a solvent such as hot toluene.

The compounds (IIb) for which R$_1$=(C$_1$-C$_6$)alkyl may be obtained from compounds (IIa) for which R$_1$=H via alkylation, for example using a dialkylsulfate, by analogy to a procedure described in the literature (G. W. Rewcastle et al., J. Med. Chem. (1994), 37, 2033).

The 2-oxindoles of general formula (IIa) are known in the literature or are commercially available.

Synthetic Pathway for Carboxylic Esters (n=0; Y=OR$_3$)

As illustrated in scheme 2, the 2-chloroindole of general formula (IV), where X and R$_1$ are as defined above, is converted to pyrimido[4,5-b]indol-4-one (V) by treatment with thionyl chloride, then by addition of an alkyl, heteroalkyl, aryl or heteroaryl amidine of general formula R$_2$C(NH)NH$_2$ in which R$_2$ is as defined above and finally by heating in a high-boiling-point solvent such as diphenyl ether for example. The pyrimido[4,5-b]indol-4-one (V) may also be obtained from 2-aminoindole of general formula (VI) where X and R$_1$ are as defined above and R is a (C$_1$-C$_6$)alkyl, by making it react with a cyanoaryl or cyanoheteroaryl derivative of general formula R$_2$CN in which R$_2$ is as defined above, in the presence of a base such as sodium hydride in a polar aprotic solvent such as tetrahydrofuran, when hot.

The pyrimido[4,5-b]indol-4-one of general formula (V), in which X, R$_1$ and R$_2$ are as defined above, is then converted to a triflate of general formula (VII), in which X, R$_1$ and R$_2$ are as defined above and OTf is a triflate group, for example in the presence of trifluoromethanesulfonic anhydride in a solvent such as dichloromethane. The ester of general formula (I), in which X, R$_1$, R$_2$ and R$_3$ are as defined above, is finally obtained by a carbonylation reaction of the triflate of general formula (VII), for example in the presence of a catalyst such as palladium acetate, carbon monoxide, a ligand of phosphine type such as 1,3-bis(diphenylphosphino)propane and an alcohol of general formula R$_3$OH, in which R$_3$ is as defined above.

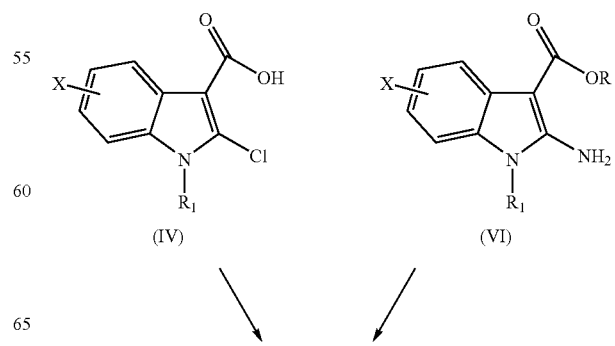

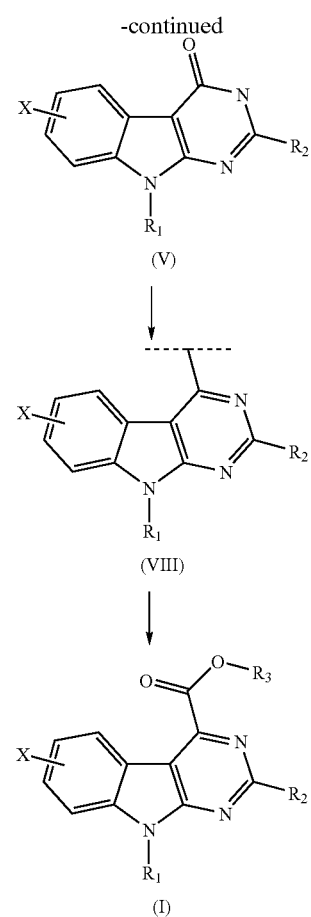

(V)

(VIII)

(I)
(n = 0, Y = OR₃)

The ester of general formula (I), in which n=0; Y=OR₃, R₁=(C₁-C₆)alkyl, X, R₂ and R₃ being as defined above, may also be obtained from the corresponding amide of general formula (I) in which n=0, Y=NR₄R₅, R₁=(C₁-C₆)alkyl, X, R₂, R₄ and R₅ being as defined above, for example when R₄ and R₅ represent, independently of one another, a methyl via action at high temperature of an acid such as sulfuric acid in an alcohol of general formula R₃OH, in which R₃ is as defined above.

The amides of general formula (I) in which n=0, Y=NR₄R₅, X, R₁, R₂, R₄ and R₅ being as defined above, may also be obtained from an ester of general formula (I) in which n=0, Y=OR₃, R₃=(C₁-C₆)alkyl, X, R₁ and R₂ being as defined above, via action of an amine of general formula HNR₄R₅, in which R₄ and R₅ are as defined above, for example in the presence of a trialkylaluminum derivative in a solvent such as toluene.

The acids of general formula (I) in which n=0, Y=OR₃, R₃=H, X, R₁, R₂ being as defined above, may be obtained by saponification of the corresponding esters for which R₃=(C₁-C₆)alkyl, for example in the presence of a base such as lithium hydroxide monohydrate in a solvent such as a mixture of tetrahydrofuran, methanol and water.

The amides of general formula (I) in which n=0, Y=NR₄R₅, X, R₁, R₂, R₄ and R₅ being as defined above, may also be obtained by coupling the corresponding acids of general formula (I) in which n=0, Y=OR₃ and R₃=H with an amine of general formula HNR₄R₅ as defined above, according to methods known to a person skilled in the art.

Synthetic Pathway for Acetamides (n=1, Y=NR₄R₅)

According to scheme 3, a pyrimido[4,5-b]indol-4-one derivative of general formula (V) as defined above, is converted to a 4-halopyrimido[4,5-b]indole of general formula (VIII) where X, R₁ and R₂ are as defined above and Hal is a halogen atom, by using a halogenating agent, for example oxalyl chloride in a polar aprotic solvent such as N,N-dimethylformamide, at high temperature. The compound of general formula (VIII) may then be condensed with a malonate of general formula R'O(CO)CH₂(CO)NR₄R₅, in which R₄ and R₅ are as defined above and R' is a (C₁-C₆)alkyl, in the presence of a base and a metal salt such as a copper salt resulting in a compound of general formula (IX) in which X, R₁, R₂, R₄, R₅ and R' are as defined above.

Finally, the derivative of general structure (IX) may be saponified and decarboxylated by using, for example, lithium hydroxide, in a mixture of methanol, water and an ethereal solvent, to result in the amide of general formula (I) in which X, R₁, R₂, R₄ and R₅ are as defined above.

Scheme 3

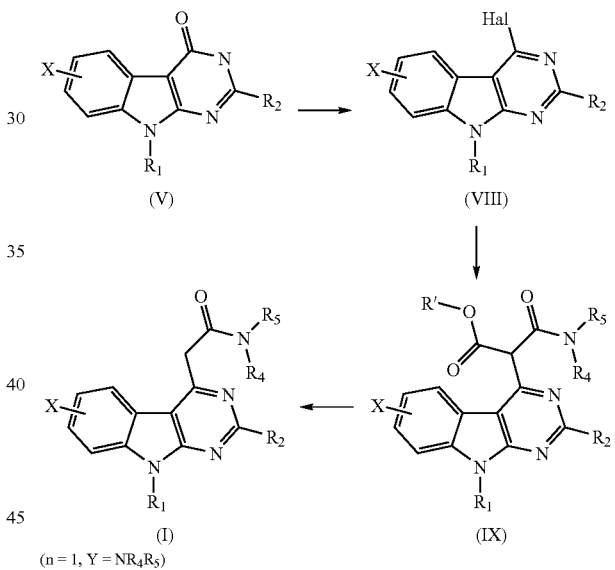

(V)  (VIII)

(I)  (IX)
(n = 1, Y = NR₄R₅)

Synthetic Pathway for Acetic Esters (n=1, Y=OR₃)

The esters of general formula (I), in which n=1, Y=OR₃, R₁=(C₁-C₆)alkyl, R₂ and R₃ being as defined above, may be obtained from the corresponding amide of general formula (I) in which n=1, Y=NR₄R₅, R₁=(C₁-C₆)alkyl, R₂, R₄ and R₅ being as defined above, for example when R₄ and R₅ represent, independently of one another, a methyl, via action of an acid such as sulfuric acid in a hot alcohol-based solvent.

The acids of general formula (I) in which n=1, Y=OR₃, R₃=H, R₁, R₂ being as defined above, may be obtained from the corresponding esters for which R₃=(C₁-C₆)alkyl, for example in the presence of a base such as lithium hydroxide monohydrate in a solvent such as a mixture of tetrahydrofuran, methanol and water.

The starting compounds of general formula (IIa), (IIb), (IV) and (VI), when their method of preparation is not described, are commercially available or are described in the literature, or else may be prepared according to the methods which are described therein or which are known to a person skilled in the art.

The 2-chloroindoles of general formula (IV), for which X=H, are described in the literature (by way of example, mention may be made of: H. D. H. Showalter et al., J. Med. Chem. (1997), 40, 413; P. Kutschy et al., Tetrahedron (2002), 58, 9029). The 2-chloroindoles of general formula (IV) for which X is other than H may be obtained from the 2-oxindoles of general formula (IIb) by analogy to methods described in the literature (by way of example, mention may be made of: L. Sun et al., J. Heterocyclic Chem. (1997), 34, 1399) under Vilsmeier type reaction conditions, then via oxidation of the aldehyde obtained.

The 2-aminoindoles of general formula (VI), for which $R_1$=H, are described or prepared by methods known in the literature (by way of example, mention may be made of: A. Suga et al., JP 2002 155083, A. Suga et al., WO 0174817; K. L. Munshi et al., J. Heterocyclic Chem. (1977), 14, 1145; C. A. Grob et al., Helv. Chim. Acta, (1961), 44, 1748; I. T. Forbes et al., J. Chem. Soc. Perkin Trans. 1, (1992), 275). The aminoindoles of general formula (VI), for which $R_1$ is other than H, are described in the case where X=H and $R_1$=Me (R. A. Glennon et al., J. Heterocyclic Chem. (1975), 12, 135). The aminoindoles of general formula (VI), for which $R_1$ is other than H, may be obtained by an alkylation reaction from 2-aminoindoles of general formula (VI) for which $R_1$=H by analogy to methods described in the literature (by way of example, mention may be made of: I. T. Forbes et al., J. Chem. Soc. Perkin Trans. 1, (1992), 275; R. A. Glennon et al., J. Heterocyclic Chem. (1975), 12, 135).

The carboxamidines are known in the literature or else may be prepared according to methods which are described therein or which are known to a person skilled in the art, for example the production of carboxamidine from nitrile. By way of example, mention may be made of the pyrazine-2-carboxamidine described in: J. K. Chakrabarti et al., EP 455 356.

The malonates of general formula R'O(CO)CH$_2$(CO)NR$_4$R$_5$ are known in the literature and may be prepared according to the methods which are described therein. Mention will be made, by way of example, of: W. Sucrow et al., Chem. Berichte (1968), 101(12), 4230.

The amines of general formula HNR$_4$R$_5$ are commercially available or are described in the literature. By way of example, the amines for which R$_4$ and R$_5$ form a piperidinyl ring substituted by an azetidinyl group may be prepared by analogy to a method described in the literature (P. C. Ting et al., Bioorg. Med. Chem. Lett. (2001), 11, 491).

According to another of these aspects, another subject of the invention is the compounds of formulae (III), (VII) and (IX). These compounds are useful as intermediates for synthesizing compounds of formula (I).

The examples which follow illustrate the preparation of some compounds of the invention. These examples are not limiting and only illustrate the present invention. The numbers of the compounds exemplified reflect those given in the table below, which illustrates the chemical structures and the physical properties of some compounds according to the invention. The elementary microanalyses and the IR and NMR spectra confirm the structures of the compounds obtained.

EXAMPLE 1

Compound No. 16

7-chloro-N,N,9-trimethyl-2-pyridin-3-yl-9H-pyrimido[4,5-b]indole-4-carboxamide

1.1. 6-chloro-1-methyl-1,3-dihydro-2H-indol-2-one 20 g (0.119 mol) of 6-chloro-1,3-dihydro-2H-indol-2-one were introduced into 600 ml of water. Next, 17 ml (0.180 mol) of dimethyl sulfate and 7.2 g (0.180 mol) of sodium hydroxide pellets were added. The mixture was heated at 100° C. for 20 min. The hot mixture was filtered. The insoluble part containing the starting oxindole was kept. The filtrate was cooled with an ice bath, then it was filtered. A white solid was recovered that was rinsed with water. The insoluble part obtained in the first filtration was added to the filtrate, then 17 ml (0.180 mol) of dimethyl sulfate and 7.2 g (0.180 mol) of sodium hydroxide pellets were added. The mixture was brought to 100° C. for 20 min. The hot mixture was filtered. The insoluble part was kept. The filtrate was cooled with an ice bath, then it was filtered. A white solid was recovered that was rinsed with water. This cycle was then repeated 3 times. At the end, the solids obtained from the various filtrations were combined and they were dried under vacuum in the presence of phosphorus pentoxide. The solid was purified by chromatography on a column of neutral alumina gel with a mixture of solvents (petroleum ether/dichloromethane: 20/80).

9.8 g of 6-chloro-1-methyl-1,3-dihydro-2H-indol-2-one were isolated in the form of a white solid.

M.P.: 116-117° C.

1.2. 2-(2,6-dichloro-1-methyl-1H-indol-3-yl)-N,N-dimethyl-2-oxoacetamide 5.4 ml (63 mmol) of oxalyl chloride were introduced under nitrogen into 100 ml of dichloromethane. Next, a solution of 5.0 g (27.5 mmol) of 6-chloro-1-methyl-1,3-dihydro-2H-indol-2-one, obtained in step 1.1, in 30 ml of dichloromethane was slowly added. The mixture was heated under reflux for 4 h. The mixture was cooled, then concentrated under reduced pressure. Under nitrogen, the residue was dissolved in 200 ml of dichloromethane, then the mixture was cooled to 0° C. The reaction medium was saturated with gaseous dimethylamine until a basic pH was obtained. After stirring for 15 min, the mixture was concentrated under reduced pressure. The residue was purified by chromatography on a silica gel column with a mixture of solvents (dichloromethane/methanol: 100/0 to 99/1).

5.0 g of compound was isolated in the form of a white solid.

M.P.: 146-148° C.

1.3. 7-chloro-N,N,9-trimethyl-2-pyridin-3-yl-9H-pyrimido[4,5-b]indole-4-carboxamide 0.3 g (13 mmol) of sodium was dissolved under nitrogen in 100 ml of absolute ethanol. Next, 1.0 g (6.34 mmol) of pyridine-3-carboxamidine hydrochloride was added. After stirring for 2 h, the mixture was concentrated under reduced pressure. Dichloromethane was added and it was filtered. The filtrate was concentrated under reduced pressure. Added to the residue were 100 ml of xylene, then 0.34 g (1.13 mmol) of 2-(2,6-dichloro-1-methyl-1H-indol-3-yl)-N,N-dimethyl-2-oxoacetamide obtained in step 1.2. The mixture was heated under reflux for 18 h. Then it was cooled and concentrated under reduced pressure. Dichloromethane, water and a (1M) aqueous solution of sodium hydroxide was added. The organic phase was decanted then washed with water, dried over sodium sulfate, filtered and concentrated under reduced pressure. The residue was purified by chromatography on a silica gel column with a mixture of solvents (dichloromethane/ethyl acetate: 80/20 to 0/100). The compound obtained was recrystallized in a dichloromethane/ethyl acetate mixture, it was isolated by filtration, rinsed with diethyl ether and dried under reduced pressure.

0.18 g of 7-chloro-N,N,9-trimethyl-2-pyridin-3-yl-9H-pyrimido[4,5-b]indole-4-carboxamide was isolated in the form of a white solid.

M.P.: 283-284° C. LC/MS: M$^+$H=366. $^1$H NMR (CDCl$_3$, 200 MHz): 9.8 (s, 1H); 8.9 (m, 1H); 8.7 (m, 1H); 8.1 (d, 1H); 7.3-7.5 (m, 3H); 4.0 (s, 3H); 3.5 (s, 3H); 3.1 (s, 3H).

EXAMPLE 2

Compound No. 15

7-chloro-N,N,9-trimethyl-2-pyridin-4-yl-9H-pyrimido[4,5-b]indole-4-carboxamide 2.1. pyridine-4-carboxamidine 0.44 g (19 mmol) of sodium was dissolved under nitrogen in 100 ml of methanol. Next, 3.0 g (19 mmol) of pyridine-4-carboxamidine hydrochloride dissolved in 50 ml of methanol was added. After stirring for 30 minutes, the mixture was concentrated under reduced pressure. 150 ml of chloroform were added to the residue and the mixture was heated under reflux. It was then filtered over celite™. The filtrate was cooled and concentrated under reduced pressure.

2.25 g of pyridine-4-carboxamidine was obtained in the form of a white solid.

M.P.: 136-140° C.

2.2. 7-chloro-N,N,9-trimethyl-2-pyridin-4-yl-9H-pyrimido[4,5-b]indole-4-carboxamide A solution of 2.75 g (9.4 mmol) of 2-(2,6-dichloro-1-methyl-1H-indol-3-yl)-N,N-dimethyl-2-oxoacetamide, obtained according to step 1.2. from example 1, and 4.2 g (34.6 mmol) of pyridine-4-carboxamidine obtained according to step 2.1. in 40 ml of N,N-dimethylformamide and 10 ml of 1,4-dioxane were heated at 130° C. for 6 h. After returning to ambient temperature a compound precipitated. It was isolated by filtration and rinsed with ethyl acetate. The solid was recrystallized in an ethyl acetate/methanol mixture. It was then purified by chromatography on a silica gel column with a mixture of solvents (dichloromethane/methanol: 98/2). A white solid was recovered that was recrystallized in an ethyl acetate/methanol mixture, then isolated by filtration, rinsed with diethyl ether and dried under reduced pressure.

1.1 g of 7-chloro-N,N,9-trimethyl-2-pyridin-4-yl-9H-pyrimido[4,5-b]indole-4-carboxamide was isolated in the form of a white solid.

M.P.: 268-269° C. LC/MS: M$^+$H=366 $^1$H NMR (CDCl$_3$, 200 MHz): 8.8 (d, 2H); 8.5 (d, 2H); 8.1 (d, 1H); 7.5 (d, 1H); 7.3 (dd, 1H); 4.0 (s, 3H); 3.5 (s, 3H); 3.1 (s, 3H).

EXAMPLE 3

Compound No. 18

7-chloro-N,N,9-trimethyl-2-pyrazin-2-yl-9H-pyrimido[4,5-b]indole-4-carboxamide 0.6 g (26 mmol) of sodium was dissolved under nitrogen in 150 ml of absolute ethanol. Next, 1.2 g (7.6 mmol) of pyrazine-2-carboxamidine hydrochloride was added. After stirring for 1 h 30 min, the residual insoluble part was isolated by filtration and the filtrate was concentrated under reduced pressure. 150 ml of dichloromethane was added and the mixture was filtered. The filtrate was concentrated under reduced pressure. Added to the residue were 100 ml of xylene, then 0.24 g (0.80 mmol) of 2-(2,6-dichloro-1-methyl-1H-indol-3-yl)-N,N-dimethyl-2-oxoacetamide, obtained according to step 1.2. from example 1. The mixture was heated under reflux for 18 h. It was then cooled and concentrated under reduced pressure. Dichloromethane, water and a (1M) aqueous solution of sodium hydroxide was added. The organic phase was decanted, washed with water, dried over sodium sulfate, filtered and concentrated under reduced pressure. The residue was purified by chromatography on a silica gel column with a mixture of solvents (dichloromethane/ethyl acetate: 80/20 to 0/100, then ethyl acetate/methanol: 100/0 to 95/5). The compound obtained was recrystallized in an ethyl acetate/methanol mixture, it was isolated by filtration, rinsed with diethyl ether and dried under reduced pressure.

0.070 g of 7-chloro-N,N,9-trimethyl-2-pyrazin-2-yl-9H-pyrimido[4,5-b]indole-4-carboxamide was isolated in the form of a white solid.

M.P.: 272-273° C. LC/MS: M$^+$H=367 $^1$H NMR (CDCl$_3$, 200 MHz): 9.9 (s, 1H); 8.9 (d, 1H); 8.7 (d, 1H); 8.1 (d, 1H); 7.6 (d, 1H); 7.4 (dd, 1H); 4.1 (s, 3H); 3.4 (s, 3H); 3.1 (s, 3H).

EXAMPLE 4

Compound No. 14

7-chloro-9-methyl-2-pyridin-4-yl-4-(pyrrolidin-1-ylcarbonyl)-9H-pyrimido[4,5-b]indole 4.1. 1-(2,6-dichloro-1-methyl-1H-indol-3-yl)-2-oxo-2-pyrrolidin-1-ylethanone 5.0 ml (58.2 mmol) of oxalyl chloride was introduced under nitrogen into 120 ml of dichloromethane. Next, a solution of 3.0 g (16.5 mmol) of 6-chloro-1-methyl-1,3-dihydro-2H-indol-2-one, obtained in step 1.1 from example 1, in 30 ml of dichloromethane was slowly added. The mixture was heated under reflux for 4 h. The mixture was cooled, then concentrated under reduced pressure. Under nitrogen, the residue was dissolved in 150 ml of dichloromethane and the mixture was cooled to 0° C. Next, 2.8 ml (33.8 mmol) of pyrrolidine were slowly added. After stirring for around 15 min, a 1M aqueous solution of hydrochloric acid was added up to a pH of 3-4. The organic phase was decanted, washed with water, dried over sodium sulfate, filtered and concentrated under reduced pressure. The residue was purified by chromatography on a silica gel column with a mixture of solvents (dichloromethane/ethyl acetate: 95/5 to 70/30). The solid obtained was recrystallized in a dichloromethane/ethyl acetate mixture, isolated by filtration, rinsed with diethyl ether and dried under reduced pressure.

3.3 g of 1-(2,6-dichloro-1-methyl-1H-indol-3-yl)-2-oxo-2-pyrrolidin-1-ylethanone was isolated in the form of a white solid.

M.P.: 174-175° C.

4.2. 7-chloro-9-methyl-2-pyridin-4-yl-4-(pyrrolidin-1-ylcarbonyl)-9H-pyrimido[4,5-b]indole A solution of 1.0 g (3.07 mmol) of 1-(2,6-dichloro-1-methyl-1H-indol-3-yl)-2-oxo-2-pyrrolidin-1-ylethanone, obtained in step 4.1, and 1.3 g (10.6 mmol) of pyridine-4-carboxamidine, obtained in step 2.1 from example 2, in 60 ml of xylene were heated under reflux for 5 h. After returning to ambient temperature, the mixture was concentrated under reduced pressure. 200 ml of dichloromethane was added, the organic phase was washed with a saturated sodium hydrogencarbonate aqueous solution, then with water. The organic phase was dried over sodium sulfate, filtered and concentrated under reduced pressure. The residue was purified by chromatography on a silica gel column with a mixture of solvents (dichloromethane/ethyl acetate: 90/10 to 0/100). A white solid was recovered that was recrystallized in a dichloromethane/ethyl acetate mixture, then isolated by filtration, rinsed with diethyl ether and dried under reduced pressure.

0.40 g of 7-chloro-9-methyl-2-pyridin-4-yl-4-(pyrrolidin-1-ylcarbonyl)-9H-pyrimido[4,5-b]indole was isolated in the form of a white solid.

M.P.: 256-258° C. LC/MS: M+H=392. $^1$H NMR (CDCl$_3$, 300 MHz): 8.8 (m, 2H); 8.5 (m, 2H); 8.4 (d, 1H); 7.5 (d, 1H); 7.4 (d, 1H); 4.0 (s, 3H); 3.9 (t, 2H); 3.8 (t, 2H); 2.1-1.9 (m, 4H).

EXAMPLE 5

Compound No. 5

7-chloro-N,N-dimethyl-2-phenyl-9H-pyrimido[4,5-b]indole-4-carboxamide

5.1. 2-(2,6-dichloro-1H-indol-3-yl)-N,N-dimethyl-2-oxoacetamide

Under nitrogen, 8 ml (91.7 mmol) of oxalyl chloride were introduced into 150 ml of dichloromethane. Next, 5.0 g (29.8 mmol) of 6-chloro-1,3-dihydro-2H-indol-2-one were added in small portions. The mixture was stirred for 2 h at ambient temperature, then 4 h under reflux. The mixture was cooled, then concentrated under reduced pressure. Under nitrogen, the residue was dissolved in 150 ml of dichloromethane and the mixture was cooled to 0° C. The reaction medium was saturated with gaseous dimethylamine until a basic pH was obtained. After stirring for 15 min, a 1M aqueous solution of hydrochloric acid was added until a pH of 2-3. Next, 300 ml of dichloromethane and 100 ml of water were added. The organic phase was decanted, washed with water, dried over sodium sulfate, filtered and concentrated under reduced pressure. The residue was purified by chromatography on a silica gel column with a mixture of solvents (dichloromethane/ethyl acetate: 90/10 to 50/50). The solid obtained was rinsed with diethyl ether and dried under reduced pressure.

3.2 g of 2-(2,6-dichloro-1H-indol-3-yl)-N,N-dimethyl-2-oxoacetamide was isolated in the form of a white solid.

M.P.: 223-224° C.

5.2. 7-chloro-N,N-dimethyl-2-phenyl-9H-pyrimido[4,5-b]indole-4-carboxamide

Under nitrogen, 0.2 g (8.3 mmol) of sodium were dissolved in 100 ml of absolute ethanol. Next, 1.0 g (6.38 mmol) of benzamidine hydrochloride were added. After stirring for 30 minutes, the mixture was concentrated under reduced pressure. Dichloromethane was added and the mixture was filtered. The filtrate was concentrated under reduced pressure. Added to the residue were 120 ml of toluene, then 0.30 g (1.2 mmol) of 2-(2,6-dichloro-1H-indol-3-yl)-N,N-dimethyl-2-oxoacetamide, obtained in step 5.1. from example 5. The mixture was heated under reflux for 18 h. Then it was cooled and concentrated under reduced pressure. Dichloromethane and water were added. The organic phase was decanted, washed with water, dried over sodium sulfate, filtered and concentrated under reduced pressure. The residue was purified by chromatography on a silica gel column with a mixture of solvents (dichloromethane/ethyl acetate: 95/5 to 50/50). The compound obtained was recrystallized in a dichloromethane/ethyl acetate mixture, isolated by filtration, rinsed with diethyl ether and dried under reduced pressure.

0.09 g of 7-chloro-N,N-dimethyl-2-phenyl-9H-pyrimido[4,5-b]indole-4-carboxamide were isolated in the form of a white solid.

M.P.: 232-233° C. LC/MS: M+H=351 $^1$H NMR (DMSO-d$_6$, 200 MHz): 12.7 (s, 1H); 8.5 (m, 2H); 7.9 (d, 1H); 7.5-7.6 (m, 4H); 7.4 (dd, 1H); 3.2 (s, 3H); 3.0 (s, 3H).

EXAMPLE 6

Compound No. 4

6-chloro-N,N,9-trimethyl-2-phenyl-9H-pyrimido[4,5-b]indole-4-carboxamide

6.1. 5-chloro-1-methyl-1,3-dihydro-2H-indol-2-one 13.3 g (0.795 mol) of 5-chloro-1,3-dihydro-2H-indol-2-one were introduced into 200 ml of water. Next, 120 ml of a 1M solution of sodium hydroxide and 11.3 ml (0.120 mol) of dimethyl sulfate were added. The mixture was heated to 120° C. for 30 min. It was left to cool, then 4.81 g (120 mmol) of sodium hydroxide and 11.3 ml (0.120 mol) of dimethyl sulfate were added. The mixture was heated to 120° C. for 30 min. It was left to cool and the operation was repeated once more. Next, the reaction mixture was filtered and the precipitate was rinsed with water and dried under vacuum in the presence of phosphorus pentoxide. 250 ml of dichloromethane were added to the filtrate. The organic phase was decanted, washed with water, dried over sodium sulfate, filtered and concentrated under reduced pressure. The precipitate was added to the residue obtained and the assembly was purified by chromatography on a neutral alumina gel column with a mixture of solvents (dichloromethane/ethyl acetate: 98/2 to 50/50).

3.9 g of 5-chloro-1-methyl-1,3-dihydro-2H-indol-2-one were isolated in the form of a white solid.

M.P.: 118-119° C.

6.2. 2-(2,5-dichloro-1-methyl-1H-indol-3-yl)-N,N-dimethyl-2-oxoacetamide

Under nitrogen, 8.1 ml (92.8 mmol) of oxalyl chloride were introduced into 150 ml of dichloromethane. Next, 3.9 g (30.7 mmol) of 5-chloro-1-methyl-1,3-dihydro-2H-indol-2-one, obtained in step 6.1. from example 6, were added in small portions. The mixture was heated under reflux for 4 h. The mixture was cooled, then concentrated under reduced pressure. The residue was dissolved under nitrogen in 120 ml of dichloromethane and the mixture was cooled to 0° C. The reaction medium was saturated with gaseous dimethylamine until a basic pH was obtained. After stirring for 15 min, the mixture was concentrated under reduced pressure. The following were added: 250 ml of dichloromethane, 100 ml of water and a 1M aqueous solution of hydrochloric acid up to a pH of 3-4. The organic phase was decanted, washed with water, dried over sodium sulfate, filtered and concentrated under reduced pressure. The residue was purified by chromatography on a silica gel column with a mixture of solvents (dichloromethane/ethyl acetate: 95/5 to 50/50).

1.45 g of 2-(2,5-dichloro-1-methyl-1H-indol-3-yl)-N,N-dimethyl-2-oxoacetamide were isolated in the form of a white solid.

M.P.: 205-206° C.

6.3. 6-chloro-N,N,9-trimethyl-2-phenyl-9H-pyrimido[4,5-b]indole-4-carboxamide Under nitrogen, 0.34 g (14.8 mmol) of sodium were dissolved in 120 ml of absolute ethanol. Next, 2.0 g (12.8 mmol) of benzamidine hydrochloride were added. After stirring for 30 minutes, the mixture was concentrated under reduced pressure. Dichloromethane was added and the mixture was filtered. The filtrate was concentrated under reduced pressure. Added to the residue were 60 ml of xylene, then 0.90 g (3 mmol) of 2-(2,5-dichloro-1-methyl-1H-indol-3-yl)-N,N-dimethyl-2-oxoacetamide, obtained in step 6.2. from example 6. The mixture was heated under reflux for 3 h. Then it was cooled and concentrated under reduced pressure. Dichloromethane and water were added. The organic phase was decanted, washed with water, dried over sodium sulfate, filtered and concentrated under reduced pressure. The residue was purified by chromatography on a silica gel column with a mixture of solvents (dichloromethane/ethyl acetate: 95/5 to 50/50). The compound obtained was recrystallized in a dichloromethane/ethyl acetate mixture, isolated by filtration, rinsed with diethyl ether and dried under reduced pressure.

0.53 g of 6-chloro-N,N,9-trimethyl-2-phenyl-9H-pyrimido[4,5-b]indole-4-carboxamide were isolated in the form of a white solid.

M.P.: 222-224° C. LC/MS: M$^+$H=365. $^1$H NMR (CDCl$_3$, 200 MHz): 8.7 (m, 2H); 8.1 (d, 1H); 7.6-7.5 (m, 4H); 7.4 (d, 1H); 4.1 (s, 3H); 3.4 (s, 3H); 3.2 (s, 3H).

EXAMPLE 7

Compound No. 23

N,N-dimethyl-2-phenyl-9H-pyrimido[4,5-b]indole-4-carboxamide

7.1. 2-(2-chloro-1H-indol-3-yl)-N,N-dimethyl-2-oxoacetamide

Under nitrogen, 7.9 ml (90.5 mmol) of oxalyl chloride were introduced into 150 ml of dichloromethane. Next, 6.0 g (45 mmol) of 1,3-dihydro-2H-indol-2-one were added in small portions. The mixture was stirred at ambient temperature for 4 h. Next, the solid was filtered and dissolved in 150 ml of dichloromethane. The mixture was cooled to 0° C. The reaction medium was saturated with gaseous dimethylamine until a basic pH was obtained. After stirring for 5 minutes, the mixture was concentrated under reduced pressure. The residue was purified by chromatography on a silica gel column with a mixture of solvents (dichloromethane/ethyl acetate: 95/5 to 50/50).

2.46 g of 2-(2-chloro-1H-indol-3-yl)-N,N-dimethyl-2-oxoacetamide were isolated in the form of a white solid.

M.P.: 197-198° C.

7.2. N,N-dimethyl-2-phenyl-9H-pyrimido[4,5-b]indole-4-carboxamide

Under nitrogen, 0.40 g (17.4 mmol) of sodium were dissolved in 100 ml of methanol. Next, 2.72 g (17.4 mmol) of benzamidine hydrochloride were added. After stirring for 30 minutes, the mixture was concentrated under reduced pressure. Dichloromethane was added and the mixture was filtered. The filtrate was concentrated under reduced pressure. Added to the residue were 100 ml of xylene, then 1.52 g (6.1 mmol) of 2-(2-chloro-1H-indol-3-yl)-N,N-dimethyl-2-oxoacetamide obtained in step 7.1. from example 7. The mixture was heated under reflux for 5 h. Then it was cooled and concentrated under reduced pressure. Dichloromethane and water were added. The organic phase was decanted, washed with water, dried over sodium sulfate, filtered and concentrated under reduced pressure. The residue was purified by chromatography on a silica gel column with a mixture of solvents (dichloromethane/ethyl acetate: 90/10 to 70/30). The fractions containing the compound were concentrated, under reduced pressure, until the appearance of a precipitate. It was isolated by filtration, rinsed with diethyl ether and dried under reduced pressure.

1.36 g of N,N-dimethyl-2-phenyl-9H-pyrimido[4,5-b]indole-4-carboxamide were isolated in the form of a white solid.

M.P.: 218-219° C. MS: M$^+$H=317. $^1$H NMR (DMSO-d$_6$, 200 MHz): 12.6 (s, 1H); 8.5 (m, 2H); 7.9 (d, 1H); 7.6-7.5 (m, 5H); 7.3 (m, 1H); 3.2 (s, 3H); 2.9 (s, 3H).

EXAMPLE 8

Compound No. 1

N,N,9-trimethyl-2-phenyl-9H-pyrimido[4,5-b]indole-4-carboxamide

Under nitrogen, 0.40 g (1.3 mmol) of N,N-dimethyl-2-phenyl-9H-pyrimido[4,5-b]indole-4-carboxamide obtained in step 7.2. from example 7 and 1 ml (7.5 mmol) of 1,1-dimethoxytrimethylamine in 120 ml of toluene were heated under reflux for 6 h. Next, the mixture was cooled to room temperature and concentrated under reduced pressure. The residue was purified by chromatography on a silica gel column with a mixture of solvents (dichloromethane/ethyl acetate: 100/0 to 50/50). The fractions containing the product were combined and concentrated under reduced pressure. The compound was recrystallized in ethyl acetate, isolated by filtration, rinsed with diethyl ether and dried under reduced pressure.

0.33 g of N,N,9-trimethyl-2-phenyl-9H-pyrimido[4,5-b]indole-4-carboxamide were isolated in the form of a white solid.

M.P.: 193-195° C. LC/MS: M+H=331. ¹H NMR (CDCl₃, 200 MHz): 8.7 (m, 2H); 8.1 (d, 1H); 7.6-7.5 (m, 5H); 7.4 (m, 1H); 4.1 (s, 3H); 3.4 (s, 3H); 3.1 (s, 3H).

EXAMPLE 9

Compound No. 3

7-fluoro-N,N,9-trimethyl-2-phenyl-9H-pyrimido[4,5-b]indole-4-carboxamide

9.1. 6-fluoro-1-methyl-1,3-dihydro-2H-indol-2-one 10.0 g (66.5 mmol) of 6-fluoro-1,3-dihydro-2H-indol-2-one were introduced into 200 ml of water. Next, 120 ml of a 1M solution of sodium hydroxide and 11.3 ml (120 mmol) of dimethyl sulfate were added. The mixture was heated to 120° C. for 40 min. After returning to ambient temperature, 150 ml of dichloromethane and water were added. The organic phase was decanted, washed with water, dried over sodium sulfate, filtered and concentrated under reduced pressure. The residue was purified by chromatography on a neutral alumina gel column with a mixture of solvents (dichloromethane/ethyl acetate: 98/2 to 80/20). The compound obtained was rinsed with diethyl ether and dried under reduced pressure.

5.1 g of 6-fluoro-1-methyl-1,3-dihydro-2H-indol-2-one were isolated in the form of a yellowish compound.

M.P.: 100-101° C.

9.2. 2-(2-chloro-6-fluoro-1-methyl-1H-indol-3-yl)-N,N-dimethyl-2-oxoacetamide Under nitrogen, 5.0 ml (58.2 mmol) of oxalyl chloride were introduced into 120 ml of dichloromethane. Next, a solution of 4.2 g (25.4 mmol) of 6-fluoro-1-methyl-1,3-dihydro-2H-indol-2-one, obtained in step 9.1 from example 9, were slowly added in small portions. The mixture was heated under reflux for 4 h. The mixture was cooled, then concentrated under reduced pressure. Under nitrogen, the residue was dissolved in 120 ml of dichloromethane and the mixture was cooled to 0° C. The reaction medium was saturated with gaseous dimethylamine until a basic pH was obtained. After stirring for 15 min, a 1M aqueous solution of hydrochloric acid was added up to a pH of 3-4. Next, 100 ml of dichloromethane was added. The organic phase was decanted, washed with water, dried over sodium sulfate, filtered and concentrated under reduced pressure. The residue was purified by chromatography on a silica gel column with a mixture of solvents (dichloromethane/ethyl acetate: 95/5 to 50/50). The fractions containing the compound were concentrated under reduced pressure until the appearance of a precipitate. It was recovered by filtration and rinsed with diethyl ether and dried under reduced pressure.

3.5 g of 2-(2-chloro-6-fluoro-1-methyl-1H-indol-3-yl)-N,N-dimethyl-2-oxoacetamide were isolated in the form of a white compound.

M.P.: 175-177° C.

9.3. 7-fluoro-N,N,9-trimethyl-2-phenyl-9H-pyrimido[4,5-b]indole-4-carboxamide Under nitrogen, 0.28 g (12.17 mmol) of sodium were dissolved in 120 ml of methanol. Next, 1.89 g (12.07 mmol) of benzamidine hydrochloride were added. After stirring for 30 minutes, the mixture was concentrated under reduced pressure. Dichloromethane was added and the mixture was filtered. The filtrate was concentrated under reduced pressure. Added to the residue were 50 ml of xylene, then 0.80 g (2.8 mmol) of 2-(2-chloro-6-fluoro-1-methyl-1H-indol-3-yl)-N,N-dimethyl-2-oxoacetamide, obtained in step 9.2. from example 9. The mixture was heated under reflux for 6 h. Then it was cooled and concentrated under reduced pressure. Dichloromethane and water were added. The organic phase was decanted, washed with water, dried over sodium sulfate, filtered and concentrated under reduced pressure. The residue was purified by chromatography on a silica gel column with a mixture of solvents (dichloromethane/ethyl acetate: 98/2 to 90/10). The fractions containing the compound were concentrated under reduced pressure until the appearance of a precipitate. It was recovered by filtration and rinsed with diethyl ether. The compound obtained was recrystallized in a dichloromethane/ethyl acetate mixture, isolated by filtration, rinsed with diethyl ether and dried under reduced pressure.

0.40 g of 7-fluoro-N,N,9-trimethyl-2-phenyl-9H-pyrimido[4,5-b]indole-4-carboxamide was isolated in the form of a white solid.

M.P.: 229-231° C. LC/MS: M+H=349. ¹H NMR (DMSO-d₆, 200 MHz): 8.6 (m, 2H); 7.9 (dd, 1H); 7.7 (dd, 1H); 7.5 (m, 3H); 7.2 (m, 1H); 4.0 (s, 3H); 3.2 (s, 3H); 3.0 (s, 3H).

EXAMPLE 10

Compound No. 24

Ethyl 7-chloro-9-methyl-2-phenyl-9H-pyrimido[4,5-b]indole-4-carboxylate

A solution of 1.6 g (4.4 mmol) of 7-chloro-N,N,9-trimethyl-2-phenyl-9H-pyrimido[4,5-b]indole-4-carboxamide, obtained according to example 16 in 80 ml of absolute ethanol and 2.5 ml of sulfuric acid was heated under reflux for 48 h. The mixture was cooled to ambient temperature and partially concentrated under reduced pressure. Next, crushed ice and dichloromethane were added. The organic phase was decanted, washed with water, dried over sodium sulfate, filtered and concentrated under reduced pressure. The residue was purified by chromatography on a silica gel column with a mixture of solvents (dichloromethane/ethyl acetate: 100/0 to 80/20). The fractions containing the compound were concentrated under reduced pressure. The residue was taken up by cyclohexane, recovered by filtration and rinsed with pentane.

0.46 g of ethyl 7-chloro-9-methyl-2-phenyl-9H-pyrimido[4,5-b]indole-4-carboxylate were isolated in the form of a white compound.

M.P.: 139-140° C. MS: M+H=366. ¹H NMR (CDCl₃, 200 MHz): 8.8 (d, 1H); 8.6 (m, 2H); 7.6-7.5 (m, 4H); 7.3 (dd, 1H); 4.7 (q, 2H); 4.0 (s, 3H); 1.6 (t, 3H).

EXAMPLE 11

Compound No. 11

7-chloro-9-methyl-4-[(4-methylpiperazin-1-yl)carbonyl]-2-phenyl-9H-pyrimido[4,5-b]indole Added to 30 ml of toluene were 4 ml (8 mmol) of a solution of trimethylaluminum (2M in toluene) under argon. The solution was cooled to 0° C., then 0.80 g (8 mmol) of 4-methylpiperazine was added in portions. Stirring was continued for 1H at ambient temperature. Next, 0.46 g (1.20 mmol) of ethyl 7-chloro-9-methyl-2-phenyl-9H-pyrimido[4,5-b]indole-4-carboxylate obtained in example 10 was added. The reaction medium was heated under reflux for 3 h. The solution was cooled to around 0° C., then water was added dropwise. Added next were dichloromethane, then a concentrated solution of sodium hydroxide. The organic phase was decanted, washed with water, dried over sodium sulfate, then filtered and concentrated under reduced pressure. The residue was purified by chromatography on a silica gel column with a mixture of solvents (dichloromethane/ethyl acetate: 50/50, then pure ethyl acetate, then ethyl acetate/methanol: 95/5). The fractions containing the compound were concentrated under reduced pressure. 0.54 g of a white compound was isolated. Added to this compound were dichloromethane and 13 ml of a 0.1N solution of hydrochloric acid in propane-2-ol. The solution was concentrated under reduced pressure. The residue was recrystallized in ethanol and rinsed with diethyl ether. Added to the compound obtained were dichloromethane then a 1M aqueous solution of sodium hydroxide. The organic phase was decanted, washed with water, dried over sodium sulfate, filtered and concentrated under reduced pressure. The residue was purified by chromatography on a silica gel column with a mixture of solvents (dichloromethane/methanol: 98/2 to 90/10). The fractions containing the compound were concentrated under reduced pressure. The compound obtained was recrystallized in a dichloromethane/ethyl acetate mixture, it was recovered by filtration, rinsed with diethyl ether and dried under reduced pressure.

0.43 g of 7-chloro-9-methyl-4-[(4-methylpiperazin-1-yl)carbonyl]-2-phenyl-9H-pyrimido[4,5-b]indole were isolated in the form of a white solid.

M.P.: 236-238° C. LC/MS: M+H=420. $^1$H NMR (CDCl$_3$, 200 MHz): 8.8 (m, 2H); 8.1 (d, 1H); 7.6-7.5 (m, 4H); 7.3 (dd, 1H); 4.1 (m, 2H); 4.0 (s, 3H); 3.6 (m, 2H); 2.7 (m, 2H); 2.5 (m, 2H); 2.4 (s, 3H).

EXAMPLE 12

Compound No. 21

2-(7-chloro-9-methyl-2-pyridin-4-yl-9H-pyrimido[4,5-b]indol-4-yl)-N,N-dimethylacetamide 12.1. Ethyl 2-amino-6-chloro-1-methyl-1H-indole-3-carboxylate Under nitrogen, 2.5 g (62.5 mmol) of sodium hydride (at 60% in mineral oil) were introduced into 200 ml of tetrahydrofuran. The mixture was cooled to 0° C. and 14.89 g (62.38 mmol) of ethyl 2-amino-6-chloro-1H-indole-3-carboxylate were added in portions. After stirring for 1 h at 0° C., 3.9 ml (62.6 mmol) of iodo-methane were added and the mixture was stirred for 12 h at ambient temperature. 3 ml of absolute ethanol was added and the mixture was concentrated under reduced pressure. The residue was purified by chromatography on a silica gel column with a mixture of solvents (dichloromethane/ethyl acetate: 98/2 to 80/20). The fractions containing the compound were concentrated under reduced pressure.

5.9 g of ethyl 2-amino-6-chloro-1-methyl-1H-indol-3-carboxylate were isolated in the form of a solid.

M.P.: 155-157° C.

12.2. 7-chloro-9-methyl-2-pyridin-4-yl-3,9-dihydro-4H-pyrimido[4,5-b]indol-4-one Under nitrogen, 0.32 g (8 mmol) of sodium hydride (at 60% in mineral oil) were introduced into 100 ml of tetrahydrofuran. The mixture was cooled to 0° C. and 2.0 g (7.91 mmol) of ethyl 2-amino-6-chloro-1-methyl-1H-indole-3-carboxylate, obtained in step 12.1. from example 12 were added. After stirring for 40 minutes at 0° C., the refrigerated bath was removed and 2 g (19.2 mmol) of 4-cyanopyridine were added. Next, the mixture was stirred at 80° C. for 18 h. The mixture was cooled to ambient temperature then it was concentrated under reduced pressure. Added to the residue were dichloromethane, water and a 1M aqueous solution of sodium hydroxide. The mixture was stirred for 2 h. An insoluble fraction was recovered by filtration, rinsed with water and dried in an oven under reduced pressure and in the presence of phosphorus pentoxide.

1.55 g of 7-chloro-9-methyl-2-pyridin-4-yl-3,9-dihydro-4H-pyrimido[4,5-b]indol-4-one were isolated in the form of a solid.

M.P.: >300° C.

12.3. 4,7-dichloro-9-methyl-2-pyridin-4-yl-9H-pyrimido[4,5-b]indole

Under nitrogen and at 0° C., 14 ml (160 mmol) of oxalyl chloride were added slowly to 120 ml of N,N-dimethylformamide. After stirring for 30 minutes, 1.55 g (5 mmol) of 7-chloro-9-methyl-2-pyridin-4-yl-3,9-dihydro-4H-pyrimido[4,5-b]indol-4-one, obtained in step 12.2. of example 12 were added at 0° C. The refrigerated bath was removed and the mixture was heated to 80° C. for 18 h. The mixture was cooled to room temperature and poured over crushed ice. Next, dichloromethane and a 30% aqueous solution of sodium hydroxide were added. After stirring, the organic phase was decanted, washed with water, dried over sodium sulfate, filtered and concentrated under reduced pressure. The residue was partially dissolved in dichloromethane. The insoluble fraction was separated by filtration and the filtrate was purified by chromatography on a silica gel column with a mixture of solvents (dichloromethane/ethyl acetate: 80/20 to 50/50). The fractions containing the compound were combined with the insoluble fraction, then they were partially concentrated under reduced pressure. A precipitate was recovered by filtration that was then rinsed with diethyl ether.

0.83 g of 4,7-dichloro-9-methyl-2-pyridin-4-yl-9H-pyrimido[4,5-b]indole were isolated in the form of a white solid.

M.P.: 272-274° C.

12.4. Ethyl 2-(7-chloro-9-methyl-2-pyridin-4-yl-9H-pyrimido[4,5-b]indol-4-yl)-3-(dimethylamino)-3-oxopropanoate Under nitrogen, 0.55 g (13.7 mmol) of sodium hydride (at 60% in mineral oil) were introduced into 150 ml of 1,4-dioxane. The mixture was cooled to 0° C. and 2.2 g (13.8 mmol) of ethyl 3-(dimethylamino)-3-oxopropanoate were slowly added. After stirring for 40 min at 0° C., 0.83 g (2.52 mmol) of 4,7-dichloro-9-methyl-2-pyridin-4-yl-9H-pyrimido[4,5-b]indole, obtained in step 12.3 from example 12, were added, then the refrigerated bath was removed. Next, 2.5 g (13.1 mmol) of copper iodide were added and the mixture was heated for 6 h under reflux. The mixture was cooled to ambient temperature and concentrated under reduced pressure. Next, dichloromethane, water and a saturated aqueous solution of sodium hydrogen carbonate were added. After stirring, the organic phase was decanted, washed with water, dried over sodium sulfate, filtered and were concentrated under reduced pressure. The residue was purified by chromatography on a silica gel column with a mixture of solvents (ethyl acetate/methanol: 100/0 to 90/10, then addition of 2% ammonia). The fractions containing the compound were partially concentrated under reduced pressure. A precipitate was isolated by filtration, rinsed with diethyl ether and dried under reduced pressure.

0.79 g of ethyl 2-(7-chloro-9-methyl-2-pyridin-4-yl-9H-pyrimido[4,5-b]indol-4-yl)-3-(dimethylamino)-3-oxopropanoate were isolated in the form of a yellowish solid.

M.P.: 224-226° C.

12.5. 2-(7-chloro-9-methyl-2-pyridin-4-yl-9H-pyrimido[4,5-b]indol-4-yl)-N,N-dimethylacetamide Over 4 h at 50° C., a solution of 0.79 g (1.85 mmol) of ethyl 2-(7-chloro-9-methyl-2-pyridin-4-yl-9H-pyrimido[4,5-b]indol-4-yl)-3-(dimethylamino)-3-oxopropanoate obtained in step 12.4 were stirred with 1.4 g (33.3 mmol) of lithium hydroxide monohydrate in a mixture of 10 ml of water, 50 ml of tetrahydrofuran and 50 ml of methanol. The mixture was cooled to ambient temperature and concentrated under reduced pressure. A solution of 35% hydrochloric acid in water was slowly added and stirred for 5 min. Next, an aqueous 30% sodium hydroxide solution was slowly added up to a basic pH. Dichloromethane was added. The organic phase was decanted. The aqueous phase was extracted with dichloromethane. The organic phases were combined, washed with water, dried over sodium sulfate, filtered and concentrated under reduced pressure. The residue was purified by chromatography on a silica gel column with a mixture of solvents (ethyl acetate/methanol: 100/0 to 90/10). The fractions containing the compound were concentrated under reduced pressure. The solid was recrystallized in an ethyl acetate/methanol mixture, and rinsed with diethyl ether.

0.19 g of 2-(7-chloro-9-methyl-2-pyridin-4-yl-9H-pyrimido[4,5-b]indol-4-yl)-N,N-dimethylacetamide were isolated in the form of a white solid.

M.P.: 231-232° C. LC/MS: M$^+$H=380. $^1$H NMR (DMSOd$_6$, 200 MHz): 8.8 (m, 2H); 8.4 (m, 2H); 8.2 (d, 1H); 8.0 (d, 1H); 7.4 (dd, 1H); 4.5 (s, 2H); 4.0 (s, 3H); 3.2 (s, 3H); 2.9 (s, 3H).

EXAMPLE 13

Compound No 19

2-(7-chloro-9-methyl-2-phenyl-9H-pyrimido[4,5-b]indol-4-yl)-N,N-dimethylacetamide 13.1. 2,6-dichloro-1H-indole-3-carbaldehyde Under nitrogen, 27 ml (292 mmol) of phosphorus oxychloride were added dropwise at 0° C. to 28 ml (366 mmol) of N,N-dimethylformamide in 190 ml of dichloromethane. The mixture was stirred for 2 h at ambient temperature. It was cooled to 0° C. and 24.5 g (146 mmol) of 6-chloro-1,3-dihydro-2H-indol-2-one were added in small portions. The mixture was stirred for 4 h at ambient temperature. It was cooled to 0° C. and 12.7 ml (146 mmol) of oxalyl chloride were added. Next, it was stirred for 12 h at ambient temperature. The mixture was cooled and 250 ml of water were added. The organic phase was decanted and washed with water (3 times). A solid precipitated from the organic phase. It was recovered by filtration and dried under reduced pressure in the presence of phosphorus pentoxide. The aqueous phases were combined and stirred for around 7 h. A solid precipitated from the aqueous phase. It was recovered by filtration and it was also dried under reduced pressure in the presence of phosphorus pentoxide. The two precipitates were combined and 16 g of 2,6-dichloro-1H-indole-3-carbaldehyde were obtained in the form of a white/beige solid.

$^1$H NMR (DMSOd$_6$, 200 MHz): 9.9 (s, 1H); 7.9 (d, 1H); 7.4 (s, 1H); 7.2 (d, 1H).

13.2. 2,6-dichloro-1-methyl-1H-indole-3-carbaldehyde

A solution of 11 g (52 mmol) of 2,6-dichloro-1H-indole-3-carbaldehyde, obtained in step 13.1, 14.7 ml (155 mmol) of dimethyl sulfate, 0.62 g (1.8 mmol) of tetramethylammonium hydrogensulfate, 770 ml of dichloromethane and 27.4 g (258 mmol) of potassium carbonate in 120 ml of water were stirred for 2 h under reflux. The mixture was cooled to ambient temperature. The organic phase was decanted. The aqueous phase was extracted with dichloromethane. The organic phases were combined and washed with water then with a saturated aqueous solution of sodium chloride. They were dried over sodium sulfate, filtered and concentrated under reduced pressure. The residue was titrated in diisopropyl ether. It was recovered by filtration and taken up in dichloromethane with a little methanol. The insoluble fraction was separated by filtration. The filtrate was partially concentrated. A solid precipitated and was recovered by filtration. The insoluble fraction and the solid were combined.

8.5 g of 2,6-dichloro-1-methyl-1H-indole-3-carbaldehyde were obtained in the form of a pale beige solid.

M.P.: 166-168° C.

13.3. 2,6-dichloro-1-methyl-1H-indole-3-carboxylic acid 10.5 g (46 mmol) of 2,6-dichloro-1-methyl-1H-indole-3-carbaldehyde, obtained according to step 13.2. from example 13, was introduced into 180 ml of dioxane and 45 ml of 2-methyl-2-butene. A solution of 20 g (221 mmol) of sodium chloride and 20 g (145 mmol) of monosodium phosphate in 120 ml of water were slowly added. The mixture was stirred for 2 h, then a solution of 5 g (55 mmol) of sodium chloride and 5 g (36 mmol) of monosodium phosphate in 30 ml of water were added. The mixture was stirred for 2 h, then a solution of 3 g (33 mmol) of sodium chloride and 3 g (22 mmol) of monosodium phosphate in 20 ml of water were added. The mixture was stirred for 3 h. 200 ml of ethyl acetate were added and it was left stirring overnight. An insoluble fraction was recovered by filtration and washed with water. The aqueous phase was extracted with ethyl acetate. The organic phases were combined and extracted with 1 M sodium hydroxide. The aqueous phase was cooled then acidified with 6 N hydrochloric acid up to a pH of 2-3. A solid precipitated. It was recovered by filtration and washed with water. It was combined with the insoluble fraction and they were dried under reduced pressure in the presence of phosphorus pentoxide.

8.7 g of 2,6-dichloro-1-methyl-1H-indole-3-carboxylic acid were obtained in the form of a yellowish white solid.

M.P.: 243-245° C.

13.4. 7-chloro-9-methyl-2-phenyl-3,9-dihydro-4H-pyrimido[4,5-b]indol-4-one 12 g (49 mmol) of 2,6-dichloro-1-methyl-1H-indole-3-carboxylic acid, obtained according to step 13.3. from example 13, were introduced into 170 ml of dioxane. 58 ml (790 mmol) of thionyl chloride were added slowly and the mixture was heated to 70° C. for 5 h. It was cooled to ambient temperature and the mixture was concentrated under reduced pressure. Toluene was added, then the mixture was concentrated under reduced pressure (2 times). Next, 300 ml of dioxane were added, the mixture was cooled to 0° C. and a solution of 25 g (208 mmol) of benzamidine in 200 ml of dioxane were added rapidly. The mixture was stirred for 12 h at ambient temperature. 50 ml of water and 300 ml of dichloromethane were added. The organic phase was decanted, dried over sodium sulfate, filtered and are concentrated under reduced pressure. 30 g of an orange-colored oil was obtained. 15 g of this oil were taken and added to 300 ml of diphenyl ether. The mixture was heated at 200° C. for 4 h. It was cooled, and the insoluble fraction was recovered by filtration and rinsed with diethyl ether. It was poured into 400 ml of dioxane and heated under reflux. A solid was recovered by hot filtration and was rinsed with dioxane. It was dried under reduced pressure in the presence of phosphorus pentoxide.

6.5 g of 7-chloro-9-methyl-2-phenyl-3,9-dihydro-4H-pyrimido[4,5-b]indol-4-one were obtained.

M.P.: >300° C.

13.5. 4-bromo-7-chloro-9-methyl-2-phenyl-9H-pyrimido[4,5-b]indole

A solution of 1.5 g (4.8 mmol) of 7-chloro-9-methyl-2-phenyl-3,9-dihydro-4H-pyrimido[4,5-b]indol-4-one, obtained in step 13.4., in 150 ml of acetonitrile were heated under reflux for 18 h in the presence of 4.0 g (13.9 mmol) of phosphorus oxybromide and 2.0 g (14.5 mmol) of potassium carbonate. The mixture was cooled to ambient temperature and the solution was poured over crushed ice. Dichloromethane and a saturated aqueous solution of potassium carbonate were added. The organic phase was filtered over celite, washed with water, dried over sodium sulfate, filtered and concentrated under reduced pressure. The residue is purified by chromatography on a silica gel column with a mixture of solvents (cyclohexane/dichloromethane: 100/0 to 50/50). The fractions containing the compound were concentrated under reduced pressure.

1.1 g of 4-bromo-7-chloro-9-methyl-2-phenyl-9H-pyrimido[4,5-b]indole were isolated in the form of a pinkish white solid.

$^1$H NMR (CDCl$_3$, 200 MHz): 8.5-8.4 (m, 2H); 8.3 (d, 1H); 7.5-7.2 (m, 5H); 3.9 (s, 3H).

13.6. Ethyl 2-(7-chloro-9-methyl-2-phenyl-9H-pyrimido[4,5-b]indol-4-yl)-3-(dimethylamino)-3-oxopropanoate 0.4 g (10 mmol) of sodium hydride (at 60% in mineral oil) was washed with pentane, then 50 ml of 1,4-dioxane were added under nitrogen. The mixture was cooled to 0° C. and 1.5 g (9.4 mmol) of ethyl 3-(dimethylamino)-3-oxopropanoate were added dropwise. The mixture was stirred for 30 min at ambient temperature and 0.80 g (2.15 mmol) of 4-bromo-7-chloro-9-methyl-2-phenyl-9H-pyrimido[4,5-b] indole, obtained in step 13.5. and 0.80 g (4.2 mmol) of copper iodide were added successively. The solution was refluxed for 20 h. It was cooled to ambient temperature and dichloromethane and water were added. The organic phase was decanted, washed with water, dried over sodium sulfate, filtered and concentrated under reduced pressure. The residue was purified by chromatography on a silica gel column with a mixture of solvents (dichloromethane/ethyl acetate: 100/0 to 95/5). The fractions containing the compound were concentrated under reduced pressure. The residue was dissolved in dichloromethane with ethyl acetate. The mixture was partially concentrated until the appearance of a precipitate. It was recovered by filtration and rinsed with diethyl ether.

1.03 g of ethyl 2-(7-chloro-9-methyl-2-phenyl-9H-pyrimido[4,5-b]indol-4-yl)-3-(dimethylamino)-3-oxopropanoate containing a minor amount of 2-(7-chloro-9-methyl-2-phenyl-9H-pyrimido[4,5-b]indol-4-yl)-N,N-dimethylacetamide were isolated in the form of a solid.

13.7. 2-(7-chloro-9-methyl-2-phenyl-9H-pyrimido[4,5-b]indol-4-yl)-N,N-dimethylacetamide A solution of 1.03 g (2.3 mmol) of ethyl 2-(7-chloro-9-methyl-2-phenyl-9H-pyrimido[4,5-b]indol-4-yl)-3-(dimethylamino)-3-oxopropanoate, obtained in step 13.6, 0.80 g (19 mmol) of lithium hydroxide in a mixture of 30 ml of tetrahydrofuran, 30 ml of methanol and 5 ml of water were heated at 50° C. for 2 h. The mixture was cooled to ambient temperature, then it was concentrated under reduced pressure. Dichloromethane, water and a 1M aqueous solution of hydrochloric acid were added. The organic phase was decanted, washed with water, dried over sodium sulfate, filtered and concentrated under reduced pressure. The residue was purified by chromatography on a silica gel column with a mixture of solvents (dichloromethane/ethyl acetate: 100/0 to 95/5). The fractions containing the compound were concentrated under reduced pressure. The residue was recrystallized in a dichloromethane/ethyl acetate mixture, it was recovered by filtration, rinsed with ethyl ether and dried under reduced pressure in the presence of phosphorus pentoxide.

0.48 g of 2-(7-chloro-9-methyl-2-phenyl-9H-pyrimido[4,5-b]indol-4-yl)-N,N-dimethylacetamide were isolated in the form of a white solid.

M.P.: 185-187° C. LC/MS: M$^+$H=379. $^1$H NMR (CDCl$_3$, 200 MHz): 8.6 (m, 2H); 8.3 (d, 1H); 7.5 (m, 4H); 7.4 (m, 1H); 4.4 (s, 2H); 4.0 (s, 3H); 3.3 (s, 3H); 3.0 (s, 3H).

EXAMPLE 14

Compound No 25

Methyl 7-chloro-9-methyl-2-phenyl-9H-pyrimido[4,5-b]indole-4-carboxylate

14.1. 7-chloro-9-methyl-2-phenyl-9H-pyrimido[4,5-b]-indol-4-yl trifluoromethanesulfonate Under nitrogen and at 0° C., 2.5 ml (14.56 mmol) of trifluoromethane sulfonic anhydride were added dropwise to a solution of 3.0 g (9.7 mmol) of 7-chloro-9-methyl-2-phenyl-3,9-dihydro-4H-pyrimido[4,5-b]indol-4-one, obtained in step 13.4. from example 13 and 4.3 ml (38.8 mmol) of pyridine in 100 ml of dichloromethane. The mixture was stirred for 15 min at 0° C., then 4 h at ambient temperature. Dichloromethane, water and a 0.1 N hydrochloric acid solution were added. The organic phase was decanted, the aqueous phase was extracted with dichloromethane. The organic phases were combined. They were dried over sodium sulfate, filtered, and concentrated under reduced pressure.

3.9 g of 7-chloro-9-methyl-2-phenyl-9H-pyrimido[4,5-b] indol-4-yl trifluoromethanesulfonate were obtained in the form of a yellowish white solid that was used as such in the following step.

14.2. Methyl 7-chloro-9-methyl-2-phenyl-9H-pyrimido[4,5-b]indole-4-carboxylate A solution of 2.5 g (5.7 mmol) of 7-chloro-9-methyl-2-phenyl-9H-pyrimido[4,5-b]indol-4-yl trifluoromethane-sulfonate, obtained in step 14.1. from example 14, 2.2 ml (14.8 mmol) of triethylamine, 30 mg (0.13 mmol) of palladium acetate, 90 mg (0.22 mmol) of 1,3-bis(diphenylphosphino)propane in 45 ml of N,N-dimethylformamide and 19 ml of methanol were heated at 70° C. under a carbon monoxide atmosphere. The solution was cooled, and the insoluble fraction was filtered and rinsed with dichloromethane. The filtrate was concentrated under reduced pressure, then it was co-evaporated with toluene under reduced pressure. Dichloromethane and water were added to the residue. The organic phase was dried over sodium sulfate, filtered and concentrated under reduced pressure. The residue was purified by chromatography on a silica gel column with a mixture of solvents (cyclohexane/dichloromethane:50/50 to 0/100). The fractions containing the compound were concentrated under reduced pressure.

0.58 g 7-chloro-9-methyl-2-phenyl-9H-pyrimido[4,5-b]-indole-4-carboxylate were isolated in the form of a white solid.

M.P.: 192-193° C. $^1$H NMR (CDCl$_3$, 200 MHz): 8.7 (d, 1H); 8.6 (m, 2H); 7.5-7.4 (m, 4H); 7.3 (dd, 1H); 4.1 (s, 3H); 3.9 (s, 3H).

EXAMPLE 15

Compound No 26

7-chloro-9-methyl-2-phenyl-9H-pyrimido[4,5-b]indole-4-carboxylic acid

A solution of 0.57 g (1.62 mmol) of 7-chloro-9-methyl-2-phenyl-9H-pyrimido[4,5-b]indole-4-carboxylate, obtained in step 14.2 from example 14 and 300 mg (7.1 mmol) of lithium hydroxide monohydrate in a mixture of 50 ml of tetrahydrofuran, 20 ml of methanol and 10 ml of water were stirred for 12 h at ambient temperature. A solution of 1 N hydrochloric acid was added up to a pH of around 1. The organic solvents were removed under reduced pressure and the precipitate obtained was recovered by filtration. It was rinsed with water then with diethyl ether and dried under reduced pressure in the presence of phosphorus pentoxide.

0.5 g of 7-chloro-9-methyl-2-phenyl-9H-pyrimido[4,5-b]indole-4-carboxylic acid were isolated in the form of a white solid.

M.P.: 208-209° C. $^1$H NMR (DMSOd$_6$, 200 MHz): 8.6-8.4 (m, 3H); 7.8 (d, 1H); 7.5-7.4 (m, 3H); 7.3 (dd, 1H); 3.9 (s, 3H).

EXAMPLE 16

Compound No 2

7-chloro-N,N,9-trimethyl-2-phenyl-9H-pyrimido[4,5-b]indole-4-carboxamide

A solution of 0.60 g (1.8 mmol) of 7-chloro-9-methyl-2-phenyl-9H-pyrimido[4,5-b]indole-4-carboxylic acid, obtained according to example 15, and 0.45 g (2.7 mmol) of carbonyldiimidazole in 100 ml of tetrahydrofuran were heated at 70° C. under a nitrogen atmosphere for 3 h. The mixture was cooled to ambient temperature and the reaction medium was saturated with gaseous dimethylamine until a basic pH was obtained, then it was stirred for 12 h at ambient temperature. The solution was concentrated under reduced pressure. Next, dichloromethane and a 0.5 N hydrochloric acid solution were added. The organic phase was washed with a saturated aqueous solution of sodium chloride, dried over sodium sulfate, filtered and concentrated under reduced pressure. The residue was purified by chromatography on a silica gel column with a mixture of solvents (dichloromethane/methanol: 100/0 to 95/5). The fractions containing the compound were concentrated under reduced pressure. The solid was recrystallized in ethyl acetate and rinsed with diethyl ether.

0.33 g of 7-chloro-N,N,9-trimethyl-2-phenyl-9H-pyrimido[4,5-b]indole-4-carboxamide were isolated in the form of a white solid.

M.P.: 211-213° C. LC/MS: M$^+$H=365. $^1$H NMR (CDCl$_3$, 200 MHz): 8.7 (m, 2H); 8.1 (d, 1H); 8.6-8.5 (m, 4H); 7.3 (dd, 1H); 4.0 (s, 3H); 3.4 (s, 3H); 3.1 (s, 3H).

EXAMPLE 17

Compound No 28

7-chloro-2-(6-methoxypyridin-3-yl)-N,N,9-trimethyl-9H-pyrimido[4,5-b]indole-4-carboxamide A solution of 490 mg (3.24 mmol) of 6-methoxypyridine-3-carboxamidine and 300 mg (1.0 mmol) of 2-(2,6-dichloro-1-methyl-1H-indol-3-yl)-N,N-dimethyl-2-oxoacetamide, obtained in step 1.2. from example 1, in 7 ml of N,N-dimethylformamide was heated at 130° C. for 2 h. The solution was cooled. The precipitate was recovered by filtration, it was rinsed with 1,4-dioxane and dried under reduced pressure. It was purified by chromatography on a silica gel column with a mixture of solvents (dichloromethane/methanol: 97/3). The compound obtained was recrystallized in an ethyl acetate/methanol mixture, filtered, rinsed with diethyl ether and dried under reduced pressure.

0.22 g of 7-chloro-2-(6-methoxypyridin-3-yl)-N,N,9-trimethyl-9H-pyrimido[4,5-b]indole-4-carboxamide were isolated in the form of a white solid.

M.P.: 267-268° C. LC/MS: M$^+$H=396. $^1$H NMR (CDCl$_3$, 200 MHz): 9.45 (d, 1H); 8.75 (dd, 1H); 8.05 (d, 1H); 7.5 (d, 1H); 7.25 (dd, 1H); 6.85 (d, 1H); 4.05 (s, 3H); 4.0 (s, 3H); 3.35 (s, 3H); 3.1 (s, 3H).

EXAMPLE 18

Compound No 41

7-chloro-2-(5-ethylpyridin-3-yl)-N,N,9-trimethyl-9H-pyrimido[4,5-b]indole-4-carboxamide A solution of 820 mg (5.50 mmol) of 5-ethylpyridin-3-carboxamidine and 400 mg (1.34 mmol) of 2-(2,6-dichloro-1-methyl-1H-indol-3-yl)-N,N-dimethyl-2-oxoacetamide, obtained in step 1.2 from example 1, in 30 ml of N,N-dimethylformamide was heated at 130° C. for 3 h. The solution was cooled. The reaction mixture was concentrated under reduced pressure. Dichloromethane was added and it was washed with water. The organic phase was dried over sodium sulfate. The mixture was filtered and concentrated under reduced pressure. The residue was purified by chromatography on a silica gel column with a mixture of solvents (dichloromethane/ethyl acetate: 90/10 to 80/20, then ethyl acetate/methanol: 100/0 to 95/5). The compound obtained was recrystallized in a dichloromethane/ethyl acetate mixture, filtered, rinsed with ethyl acetate and dried under reduced pressure.

0.18 g of 7-chloro-2-(5-ethylpyridin-3-yl)-N,N,9-trimethyl-9H-pyrimido[4,5-b]indole-4-carboxamide were isolated in the form of a pale yellow solid.

M.P.: 218-219° C. LC/MS: M+H=394. $^1$H NMR (CDCl$_3$, 200 MHz): 9.45 (d, 1H); 8.60 (m, 2H); 7.95 (d, 1H); 7.90 (d, 1H): 7.4 (dd, 1H); 4.0 (s, 3H); 3.30 (s, 3H); 3.20 (s, 3H); 2.95 (s, 3H); 2.80 (q, 2H); 1.25 (t, 3H).

EXAMPLE 19

Compound No 48

5-(7-chloro-4-dimethylcarbamoyl-9-methyl-9H-pyrimido[4,5-b]indol-2-yl)-2,3-dimethyl-pyridinium chloride A solution of 930 mg (6.23 mmol) of 5,6-dimethylpyridine-3-carboxamidine and 600 mg (2.01 mmol) of 2-(2,6-dichloro-1-methyl-1H-indol-3-yl)-N,N-dimethyl-2-oxoacetamide, obtained in step 1.2. from example 1, in 50 ml of o-xylene was heated under reflux for 5 h. The solution was cooled. The reaction mixture was concentrated under reduced pressure. Dichloromethane and a saturated aqueous solution of sodium bicarbonate were added. The organic phase was washed with water and dried over sodium sulfate. It was filtered and the filtrate was concentrated under reduced pressure. The residue was purified by chromatography on a silica gel column with a mixture of solvents (dichloromethane/ethyl acetate: from 80/20 to 0/100, then ethyl acetate/methanol: 100/0 to 95/5). After evaporation of the solvents, 340 mg (0.86 mmol) of a white solid was recovered. It was dissolved in dichloromethane and 0.35 ml (1.73 mmol) of a 5-6 N hydrochloric acid solution in isopropanol were added. The solvents were evaporated under reduced pressure and the residue was recrystallized in absolute ethanol. It was filtered, rinsed with diethyl ether and dried under reduced pressure.

0.30 g of 5-(7-chloro-4-dimethylcarbamoyl-9-methyl-9H-pyrimido[4,5-b]indol-2-yl)-2,3-dimethyl-pyridinium chloride were isolated.

M.P.: 285-289° C. LC/MS: M+H=394. $^1$H NMR (CDCl$_3$, 200 MHz): 9.4 (s, 1H); 9.05 (s, 1H); 8.0 (d, 1H); 7.90 (d, 1H); 7.45 (dd, 1H); 4.05 (s, 3H); 3.20 (s, 3H); 2.95 (s, 3H); 2.70 (s, 3H); 2.50 (s, 3H).

EXAMPLE 20

Compound No 49

3-(7-chloro-4-dimethylcarbamoyl-9-methyl-9H-pyrimido[4,5-b]indol-2-yl)-5,6,7,8-tetrahydro-quinolinium chloride A solution of 2.40 g (13.7 mmol) of 5,6,7,8-tetrahydroquinoline-3-carboxamidine and 800 mg (2.67 mmol) of 2-(2,6-dichloro-1-methyl-1H-indol-3-yl)-N,N-dimethyl-2-oxoacetamide, obtained in step 1.2 from example 1, in 70 ml of o-xylene was heated under reflux for 5 h. The solution was cooled. The reaction mixture was concentrated under reduced pressure. Dichloromethane and a saturated aqueous solution of sodium bicarbonate were added. The organic phase was washed with water, and dried over sodium sulfate. It was filtered and the filtrate was concentrated under reduced pressure. The residue was purified by chromatography on a silica gel column with a mixture of solvents (dichloromethane/ethyl acetate: from 90/10 to 0/100). After evaporation of the solvents, 870 mg (2.07 mmol) of a white solid was recovered. It was dissolved in dichloromethane and 0.83 ml (4.14 mmol) of a 5-6 N hydrochloric acid solution in isopropanol were added. The solvents were evaporated under reduced pressure and the residue was recrystallized in absolute ethanol. It was filtered, rinsed with diethyl ether and dried under reduced pressure.

0.75 g of 3-(7-chloro-4-dimethylcarbamoyl-9-methyl-9H-pyrimido[4,5-b]indol-2-yl)-5,6,7,8-tetrahydro-quinolinium chloride were isolated.

M.P.: 289-291° C. LC/MS: M+H=420. $^1$H NMR (CDCl$_3$, 200 MHz): 9.35 (s, 1H); 8.60 (s, 1H); 7.90 (d, 1H); 7.85 (d, 1H); 7.35 (dd, 1H); 4.00 (s, 3H); 3.20 (s, 3H); 2.95-2.80 (m, 7H); 1.95-1.65 (m, 4H).

EXAMPLE 21

Compound No 50

4-(7-chloro-4-dimethylcarbamoyl-9-methyl-9H-pyrimido[4,5-b]indol-2-yl)-2,6-dimethylpyridinium chloride A solution of 0.78 g (5.23 mmol) of 2,6-dimethylpyridine-4-carboxamidine and 700 mg (2.34 mmol) of 2-(2,6-dichloro-1-methyl-1H-indol-3-yl)-N,N-dimethyl-2-oxoacetamide, obtained in step 1.2 from example 1, in 30 ml of o-xylene was heated under reflux for 5 h. The solution was cooled. The reaction mixture was concentrated under reduced pressure. Dichloromethane, water and a 1 M aqueous solution of sodium hydroxide were added. The organic phase was washed with water, and dried over sodium sulfate. It was filtered and the filtrate was concentrated under reduced pressure. The residue was purified by chromatography on a silica gel column with a mixture of solvents (dichloromethane/ethyl acetate: from 80/20 to 0/100, then ethyl acetate/methanol: 100/0 to 95/5). After evaporation of the solvents, 540 mg (1.37 mmol) of a white solid was recovered. It was dissolved in dichloromethane and 0.55 ml (2.74 mmol) of a 5,6 N hydrochloric acid solution in isopropanol were added. The solvents were evaporated under reduced pressure and the residue was recrystallized in absolute ethanol. It was filtered, rinsed with diethyl ether and dried under reduced pressure.

0.69 g of 4-(7-chloro-4-dimethylcarbamoyl-9-methyl-9H-pyrimido[4,5-b]indol-2-yl)-2,6-dimethylpyridinium chloride were isolated.

M.P.: 288-292° C. LC/MS: M+H=394. $^1$H NMR (CDCl$_3$, 200 MHz): 8.50 (s, 2H); 8.00 (d, 1H); 7.95 (d, 1H); 7.45 (dd, 1H); 4.05 (s, 3H); 3.20 (s, 3H); 2.95 (s, 3H); 2.75 (s, 6H).

Table 1 below illustrates the chemical structures and the physical properties of some compounds of the invention.

In the "salt" column of this table, "—" represents a compound in free base form, whereas "HCl" represents a compound in hydrochloride form and the ratio between brackets is the acid/base ratio.

TABLE 1

(I)

| No. | n | X | Y | R₁ | R₂ | Salt | M.P. (° C.) |
|---|---|---|---|---|---|---|---|
| 1 | 0 | H | N(CH₃)₂ | CH₃ | phenyl | — | 193-195 |
| 2 | 0 | 7-Cl | N(CH₃)₂ | CH₃ | phenyl | — | 211-213 |
| 3 | 0 | 7-F | N(CH₃)₂ | CH₃ | phenyl | — | 229-231 |
| 4 | 0 | 6-Cl | N(CH₃)₂ | CH₃ | phenyl | — | 222-224 |
| 5 | 0 | 7-Cl | N(CH₃)₂ | H | phenyl | — | 232-233 |
| 6 | 0 | 7-Cl | N(CH₂CH₃)₂ | CH₃ | phenyl | — | 174-176 |
| 7 | 0 | 7-Cl | pyrrolidin-1-yl | CH₃ | phenyl | — | 210-212 |
| 8 | 0 | 7-Cl | piperidin-1-yl | CH₃ | phenyl | — | 216-218 |
| 9 | 0 | 7-Cl | morpholin-1-yl | CH₃ | phenyl | — | 214-216 |
| 10 | 0 | 7-Cl | 4-(N-azetidinyl)piperidin-1-yl | CH₃ | phenyl | — | 248-249 |
| 11 | 0 | 7-Cl | N-methylpiperazin-1-yl | CH₃ | phenyl | — | 236-238 |
| 12 | 0 | 6-Cl | N(CH₃)₂ | CH₃ | pyridin-4-yl | — | 226-227 |
| 13 | 0 | 7-F | N(CH₃)₂ | CH₃ | pyridin-4-yl | — | 272-274 |
| 14 | 0 | 7-Cl | pyrrolidin-1-yl | CH₃ | pyridin-4-yl | — | 256-258 |
| 15 | 0 | 7-Cl | N(CH₃)₂ | CH₃ | pyridin-4-yl | — | 268-269 |
| 16 | 0 | 7-Cl | N(CH₃)₂ | CH₃ | pyridin-3-yl | — | 283-284 |
| 17 | 0 | 7-Cl | N(CH₃)₂ | CH₃ | pyridin-2-yl | — | 233-235 |
| 18 | 0 | 7-Cl | N(CH₃)₂ | CH₃ | pyrazin-2-yl | — | 272-273 |
| 19 | 1 | 7-Cl | N(CH₃)₂ | CH₃ | phenyl | — | 185-187 |
| 20 | 1 | 6-Cl | N(CH₃)₂ | CH₃ | phenyl | — | 234-236 |
| 21 | 1 | 7-Cl | N(CH₃)₂ | CH₃ | pyridin-4-yl | — | 231-232 |
| 22 | 1 | 7-Cl | N(CH₃)₂ | CH₃ | pyridin-3-yl | — | 248-251 |
| 23 | 0 | H | N(CH₃)₂ | H | phenyl | — | 218-219 |
| 24 | 0 | 7-Cl | O(CH₂CH₃) | CH₃ | phenyl | — | 139-140 |
| 25 | 0 | 7-Cl | OCH₃ | CH₃ | phenyl | — | 192-193 |
| 26 | 0 | 7-Cl | OH | CH₃ | phenyl | — | 208-209 |
| 27 | 0 | 7-Cl | N(CH₃)₂ | CH₃ | 6-methylpyridin-3-yl | — | 276-277 |
| 28 | 0 | 7-Cl | N(CH₃)₂ | CH₃ | 6-methoxypyridin-3-yl | — | 267-268 |
| 29 | 0 | 7-Cl | N(CH₃)₂ | CH₃ | 2-methylpyridin-4-yl | — | 242-244 |
| 30 | 0 | 7-Cl | NCCH₃)₂ | CH₃ | 2-methoxy-pyridin-4-yl | — | 278-279 |
| 31 | 0 | 7-Cl | N(CH₃)₂ | Isobutyl | pyridin-4-yl | HCl (1/1) | 230-236 |
| 32 | 0 | 7-Cl | N(CH₃)₂ | CH₃ | cyclopropyl | — | 197-198 |
| 33 | 0 | 7-Cl | N(CH₃)₂ | CH₃ | methyl | — | 193-195 |
| 34 | 0 | 7-Cl | N(CH₃)₂ | CH₃ | isopropyl | — | 125-126 |
| 35 | 0 | 7-Cl | N(CH₃)₂ | CH₃ | tetrahydro-2H-pyran-4-yl | — | 174.5-175.5 |
| 36 | 0 | 7-Cl | N(CH₃)₂ | CH₃ | 4-[(dimethylamino)methyl]phenyl | HCl (1/1) | 257-258 |
| 37 | 0 | 7-Cl | N(CH₃)₂ | CH₃ | 6-chloropyridin-3-yl | — | 275-276 |
| 38 | 0 | 7-Cl | N(CH₃)₂ | CH₃ | 6-(trifluoromethyl)pyridin-3-yl | — | 253-255 |
| 39 | 0 | 7-Cl | N(CH₃)₂ | CH₃ | 6-ethoxypyridin-3-yl | — | 237-239 |
| 40 | 0 | 7-Cl | N(CH₃)₂ | CH₃ | 6-ethylpyridin-3-yl | — | 232-235 |
| 41 | 0 | 7-Cl | N(CH₃)₂ | CH₃ | 5-ethylpyridin-3-yl | — | 218-219 |
| 42 | 0 | 7-Cl | N(CH₃)₂ | CH₃ | 5-methylpyridin-3-yl | — | 313-314 |
| 43 | 0 | 7-Cl | N(CH₃)₂ | CH₃ | pyrimidin-5-yl | — | 322-325 |
| 44 | 0 | 7-Cl | N(CH₃)₂ | CH₃ | 5-methoxypyridin-3-yl | — | 258-260 |
| 45 | 0 | 7-Cl | N(CH₃)₂ | CH₃ | 6-(methoxymethyl)pyridin-3-yl | — | 239-241 |
| 46 | 0 | 7-Cl | N(CH₃)₂ | CH₃ | 2-methyl-1,3-thiazol-4-yl | — | 256-258 |

TABLE 1-continued (I)

| No. | n | X | Y | $R_1$ | $R_2$ | Salt | M.P. (° C.) |
|---|---|---|---|---|---|---|---|
| 47 | 0 | 7-Cl | $N(CH_3)_2$ | $CH_3$ | 6-[(dimethylamino)methyl]-pyridin-3-yl | HCl (1/1) | 240-242 |
| 48 | 0 | 7-Cl | $N(CH_3)_2$ | $CH_3$ | 5,6-dimethylpyridin-3-yl | HCl (1/1) | 285-289 |
| 49 | 0 | 7-Cl | $N(CH_3)_2$ | $CH_3$ | 5,6,7,8-tetrahydroquinolin-3-yl | HCl (1/1) | 289-291 |
| 50 | 0 | 7-Cl | $N(CH_3)_2$ | $CH_3$ | 2,6-dimethylpyridin-4-yl | HCl (1/1) | 288-292 |

The compounds of the invention were subjected to pharmacological tests which demonstrated their advantage as substances having therapeutic activities.

A Study of the Binding of [$^3$H]Ro5-4864 to Peripheral Benzodiazepine Receptors (p or PBR Sites)

The affinity of the compounds of the invention for the p or PBR sites (sites of peripheral-type binding to benzodiazepines) was determined.

The p site receptors can be labeled selectively in rat kidney membranes incubated in the presence of [$^3$H]Ro5-4864. The compounds of the invention have been the subject of an in vitro study with respect to their affinity for these receptors.

The animals used were male Sprague Dawley rats (Iffa Credo) weighing 180 to 300 mg. After decapitation, the kidney was removed and the tissue was homogenized at 4° C. using a Polytron™ homogenizer for 2 min and 6/10 of the maximum speed, in 35 volumes of 50 mM $Na_2HPO_4$ phosphate buffer, at a pH adjusted to 7.5 with $NaH_2PO_4$. The membrane homogenate was filtered over gaze and diluted 10 times with buffer.

[$^3$H]Ro5-4864 (specific activity: 70-90 Ci/mmol; New England Nuclear), at a concentration of 0.5 nM, was incubated in the presence of 100 µl of the membrane homogenate in a final volume of 1 ml of buffer containing the compound to be tested.

After an incubation of 3 h at 0° C., the membranes were recovered by filtering over Whatman GF/B™ filters washed with 2 times 4.5 ml of cold (0° C.) incubation buffer. The amount of radioactivity retained by the filter was measured by liquid scintigraphy.

For each compound concentration studied, the percentage inhibition of the binding of [$^3$H]Ro5-4864, then $IC_{50}$ concentration, the concentration which inhibits 50% of the specific binding, were determined.

The $IC_{50}$ of the most active compounds of the invention had values ranging from 1 nM to 200 nM.

Table 2 below presents the $IC_{50}$ values of some compounds according to the invention.

TABLE 2

| Compound No. | $IC_{50}$ |
|---|---|
| 2 | 2.2 nM |
| 15 | 3.1 nM |
| 19 | 1.3 nM |

The compounds of the invention were therefore ligands with an affinity for peripheral-type benzodiazepine receptors.

Study of the Neurotrophic Activity

Test of Survival of the Motor Neurons after Sectioning the Facial Nerve in Rats Aged 4 Days After lesion of the facial nerve in immature rats, the motor neurons of the facial nucleus underwent neuronal death by apoptosis. Neural survival was evaluated using histological methods and neuronal counting.

4 day old immature rats were anesthetized with pentobarbital (3 mg/kg by the i.p. route). The right facial nerve was exposed and sectioned, at its outlet from the stylomastoid foramen. After waking up, the young rats were returned to their mothers and treated for 7 days with one or two daily administrations, via oral or intraperitoneal route, at doses ranging from 1 to 10 mg/kg.

7 days after the lesion, the animals were decapitated and the brains frozen in isopentane at −40° C. The entire facial nerve was cut with a cryostat into 10 µm sections. The motor neurons were colored with cresyl violet and counted using the Histo™ software (Biocom™).

In this model, the most active compounds of the invention increased neuronal survival by about 10 to 40%.

Table 3 below presents the results for some compounds according to the invention in this model.

TABLE 3

| Compound No | % |
|---|---|
| 2 | +25* |
| 15 | +40* |
| 19 | +21* |

*via oral route, at 10 mg/kg

The results of the tests show that the most active compounds of the invention promote nerve regeneration.

The compounds of the invention may therefore be used for preparing medications intended to prevent or treat a pathology in which the peripheral-type benzodiazepine receptors are involved.

These medications find their application in therapeutics, especially in the treatment and/or prevention of peripheral neuropathies of various types, such as traumatic or ischemic neuropathies, diabetic, infectious, alcoholic, medicinal or genetic neuropathies, and also motor neurone diseases, such as spinal amyotrophies and amyotrophic lateral sclerosis. These medications also find an application in the treatment of neurodegenerative diseases of the central nervous system, either of the acute type such as cerebrovascular accidents and cranial and medular traumas, or of the chronic type such as autoimmune diseases (multiple sclerosis), Alzheimer's disease, Parkinson's disease and any other disease in which the administration of neurotrophic factors has a therapeutic effect.

The compounds of the invention may also be used for preparing medications intended for the prevention and/or treatment of anxiety, epilepsy or sleep disorders. This is because ligands of the p or PBR sites stimulate the production of neurosteroids such as pregnenolone, dehydroepiandrosterone, and 3-α-hydroxy-5-α-pregnan-20-one, by promoting the transfer of cholesterol from the outside to the inside of the mitochondrial membrane. These neurosteroids modulate the activity of the $GABA_A$-chloride channel macromolecular complex and can thus produce anxiolytic, anticonvulsant and sedative activities.

The compounds of the invention may also be used in treatments for acute or chronic renal failure, glomerulonephritis, diabetic nephropathy, cardiac ischemia and heart failure, myocardial infarction, ischemia of the lower limbs, coronary vasospasm, angina poitrineous, pathologies associated with the heart valves, inflammatory heart diseases, secondary effects due to cardiotoxic medication or as a result of heart surgery, atherosclerosis and its thromboembolic complications, restenosis, graft rejections, conditions related to an incorrect proliferation or migration of smooth muscle cells.

Furthermore, recent data from the literature indicates that the peripheral-type benzodiazepine receptor could play a fundamental role in the regulation of cell proliferation and cancerization processes. Generally, and in comparison with normal tissues, an increased density of peripheral-type benzodiazepine receptors is observed in various types of tumors and cancers.

In human astrocytomas, the expression level of the peripheral-type benzodiazepine receptor is correlated with the degree of malignicy of the tumor, the proliferation index and the survival of the patients. In human cerebral tumors, the increase of the number of peripheral-type benzodiazepine receptors is used as a diagnostic indication in medical imaging and as a therapeutic target for conjugates formed from a ligand of the peripheral-type benzodiazepine receptor and from a cytostatic drug. A high density of peripheral-type benzodiazepine receptors is also observed in ovarian carcinomas and breast cancers. Regarding the latter, it has been demonstrated that the expression level of the peripheral-type benzodiazepine receptors is linked to the aggressive potential of the tumor; furthermore, the presence of a peripheral-type benzodiazepine receptor agonist stimulates the growth of a mammary cancer line.

The combination of these results, which suggests a deleterious function of the peripheral-type benzodiazepine receptor in cancerization processes, constitutes a relevant basis for the search for synthetic ligands specific for the peripheral-type benzodiazepine receptor which are capable of blocking the effects thereof.

The compounds may therefore be used for treating tumors and cancers.

The peripheral-type benzodiazepine receptors are also present in the skin and, in this respect, the compounds that can be used according to the invention may be used for the prophylaxis or treatment of cutaneous stress.

The term "cutaneous stress" is understood to mean the various situations which might cause damage, in particular to the epidermis, regardless of the agent which causes this stress. This agent can be internal and/or external to the body, such as a chemical or radical agent, or else external such as ultraviolet radiation.

Thus the compounds that can be used according to the invention are intended to prevent and combat cutaneous irritations, dry patches, erythemas, dysesthetic sensations, heating sensations, pruritus of the skin and/or mucous membranes, or aging and may also be used in cutaneous disorders such as, for example, psoriasis, pruriginous diseases, herpes, photodermatoses, atopic dermatitis, contact dermatitis, lichens, prurigo, pruritus, insect stings, in fibroses and other disorders of collagen maturation, in immunological disorders or else in dermatological conditions such as eczema.

The compounds of the invention may also be used for preventing and treating chronic inflammatory diseases, especially rheumatoid arthritis, and pulmonary inflammatory diseases, in particular asthma, acute respiratory distress syndrome (ARDS) and chronic obstructive pulmonary disease (COPD), cystic fibrosis, bronchopulmonary diseases, lung diseases and pulmonary fibrosis).

According to one of its aspects, a subject of the invention is medication which comprises a compound of formula (I), or a pharmaceutically acceptable acid addition salt of the latter, or else a hydrate or a solvate.

According to another of its aspects, the present invention relates to pharmaceutical compositions comprising, as an active principle, a compound according to the invention. These pharmaceutical compositions contain an effective dose of at least one compound according to the invention, or one pharmaceutically acceptable salt, hydrate or solvate of said compound, and also to at least one pharmaceutically acceptable excipient.

Said excipients are chosen according to the pharmaceutical form and the method of administration desired, among the common excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its possible salt, solvate or hydrate, may be administered in unit administration form, by mixing with conventional pharmaceutical excipients, to animals and to humans for the prophylaxis or treatment of the above disorders or diseases.

Suitable unit administration forms comprise forms via oral route such as tablets, soft or hard gelatin capsules, powders, granules and oral solutions or suspensions, sublingual, buccal, intratracheal, intraocular or intranasal forms of administration, via inhalation, topical, transdermal, subcutaneous, intramuscular or intravenous forms of administration, rectal forms of administration and implants. For topical application, it is possible to use the compounds according to the invention in creams, gels, pomades or lotions.

By way of example, a unit administration form of a compound according to the invention in a form of a tablet may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropyl methyl cellulose | 2.25 mg |
| Magnesium stearate | 3.0 mg |

Said unit forms are dosed in order to allow a daily administration of 0.001 to 20 mg of active principle per kg of body weight, depending on the pharmaceutical form.

There could be particular cases where higher or lower doses are appropriate; such doses are not outside the scope of the invention. According to common practice, the appropriate dose for each patient is determined by the doctor depending on the mode of administration, the weight and the response of said patient.

The present invention, according to another of its aspects, also relates to a method of treating the pathologies indicated above which comprise the administration, to a patient, of an effective dose of a compound according to the invention, or one of its pharmaceutically acceptable salts or hydrates or solvates.

What is claimed is:

1. A compound of formula (I):

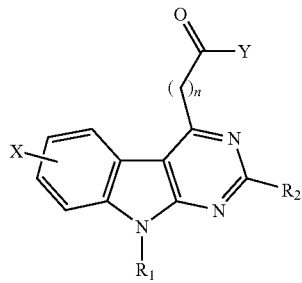

in which:
n represents the number 0 or 1;
X represents a hydrogen or halogen atom;
Y represents an $OR_3$ group or an $NR_4R_5$ group;
$R_1$ represents a hydrogen atom or a $(C_1-C_6)$alkyl group;
$R_2$ represents a $(C_1-C_6)$alkyl group, a phenyl or a monocyclic or bicyclic heterocycle, said phenyl or heterocycle groups optionally bearing one or more halogen atoms and/or one or more $(C_1-C_6)$alkyl, $(C_1-C_6)$alkoxyl, $(C_1-C_6)$alkoxy$(C_1-C_6)$alkyl, $(C_1-C_6)$alkylamino $(C_1-C_6)$alkyl or $(C_1-C_6)$dialkylamino $(C_1-C_6)$alkyl groups;
$R_3$ represents a hydrogen atom, a $(C_1-C_6)$alkyl group or a benzyl; and
$R_4$ and $R_5$ each represent, independently of one another, a hydrogen atom or a $(C_1-C_6)$alkyl group, or else $R_4$ and $R_5$ form, with the nitrogen atom that they bear, an aziridinyl, azetidinyl, pyrrolidinyl, piperidinyl, morpholinyl, thiomorpholinyl or piperazinyl, optionally substituted by a $(C_1-C_6)$alkyl, phenyl or heterocycle; or
a salt of said compound or a hydrate or a solvate of said compound or said salt.

2. The compound of formula (I) according to claim 1, wherein:
n represents the number 0 or 1;
X represents a hydrogen or halogen atom;
Y represents an $OR_3$ group or an $NR_4R_5$ group;
$R_1$ represents a hydrogen atom or a $(C_1-C_6)$alkyl group;
$R_2$ represents a phenyl or a heterocycle chosen from pyridinyl, pyrimidinyl, pyrazinyl or pyridazinyl, the phenyl or heterocycle optionally bearing one or more halogen atoms and/or one or more $(C_1-C_6)$alkyl or $(C_1-C_6)$alkoxyl groups;
$R_3$ represents a hydrogen atom, a $(C_1-C_6)$alkyl or a benzyl; and
$R_4$ and $R_5$ each represent, independently of one another, a hydrogen atom or a $(C_1-C_6)$alkyl group, or else $R_4$ and $R_5$ form, with the nitrogen atom that they bear, an aziridinyl, azetidinyl, pyrrolidinyl, piperidinyl, morpholinyl, thiomorpholinyl or piperazinyl group, optionally substituted by a $(C_1-C_6)$alkyl, phenyl or azetidinyl; or
a salt of said compound or a hydrate or a solvate of said compound or said salt.

3. The compound of formula (I) according to claim 1, wherein:
n represents the number 0 or 1;
X represents a hydrogen or fluorine or chlorine atom;
Y represents a hydroxy, $OCH_3$, $O(CH_2CH_3)$, $N(CH_3)_2$, $N(CH_2CH_3)_2$, pyrrolidinyl, piperidinyl, morpholinyl, (N-azetidinyl)piperidinyl or N-methylpiperazinyl group;
$R_1$ represents a hydrogen atom, a methyl or isobutyl group; and
$R_2$ represents a phenyl, a methyl, isopropyl or cyclopropyl group or a heterocycle chosen from pyridinyl, pyrazinyl, pyrimidinyl, thiazolyl, tetrahydroquinolinyl or tetrahydropyranyl, the phenyl and heterocycle groups optionally being substituted by one or more halogen groups and/or one or more $(C_1-C_6)$alkyl, $(C_1-C_6)$alkoxyl, $(C_1-C_6)$alkoxy$(C_1-C_6)$alkyl, $(C_1-C_6)$dialkylamino or $(C_1-C_6)$dialkylamino$(C_1-C_6)$alkyl groups; or
a salt of said compound or a hydrate or a solvate of said compound or said salt.

4. The compound of formula (I) according to claim 1 chosen from:
N,N,9-trimethyl-2-phenyl-9H-pyrimido[4,5-b]indole-4-carboxamide;
7-chloro-N,N,9-trimethyl-2-phenyl-9H-pyrimido[4,5-b]indole-4-carboxamide;
7-fluoro-N,N-9-trimethyl-2-phenyl-9H-pyrimido[4,5-b]indole-4-carboxamide;
6-chloro-N,N-9-trimethyl-2-phenyl-9H-pyrimido[4,5-b]indole-4-carboxamide;
7-chloro-N,N-dimethyl-2-phenyl-9H-pyrimido[4,5-b]indole-4-carboxamide;
7-chloro-N,N-diethyl-9-methyl-2-phenyl-9H-pyrimido[4,5-b]indole-4-carboxamide;
7-chloro-9-methyl-2-phenyl-4-(pyrrolidin-1-ylcarbonyl)-9H-pyrimido[4,5-b]indole;
7-chloro-9-methyl-2-phenyl-4-(piperidin-1-ylcarbonyl)-9H-pyrimido[4,5-b]indole;

7-chloro-9-methyl-4-(morpholin-4-ylcarbonyl)-2-phenyl-9H-pyrimido[4,5-b]indole;
4-[(4-azetidin-1-yl)piperidin-1-ylcarbonyl]-7-chloro-9-methyl-2-phenyl-9H-pyrimido-[4,5-b]indole;
7-chloro-9-methyl-4-[(4-methylpiperazin-1-yl)carbonyl]-2-phenyl-9H-pyrimido[4,5-b]indole;
6-chloro-N,N-9-trimethyl-2-pyridin-4-yl-9H-pyrimido[4,5-b]indole-4-carboxamide;
7-fluoro-N,N,9-trimethyl-2-pyridin-4-yl-9H-pyrimido[4,5-b]indole-4-carboxamide;
7-chloro-9-methyl-2-pyridin-4-yl-4-(pyrrolidin-1-ylcarbonyl)-9H-pyrimido-[4,5-b]indole;
7-chloro-N,N,9-trimethyl-2-pyridin-4-yl-9H-pyrimido[4,5-b]indole-4-carboxamide;
7-chloro-N,N,9-trimethyl-2-pyridin-3-yl-9H-pyrimido[4,5-b]indole-4-carboxamide;
7-chloro-N,N-9-trimethyl-2-pyridin-2-yl-9H-pyrimido[4,5-b]indole-4-carboxamide
7-chloro-N,N-9-trimethyl-2-pyrazin-2-yl-9H-pyrimido[4,5-b]indole-4-carboxamide;
2-(7-chloro-9-methyl-2-phenyl-9H-pyrimido[4,5-b]indol-4-yl)-N,N-dimethylacetamide;
2-(6-chloro-9-methyl-2-phenyl-9H-pyrimido]4,5-b]indol-4-yl)-N,N-dimethylacetamide;
2-(7-chloro-9-methyl-2-pyridin-4-yl-9H-pyrimido[4,5-b]indol-4-yl)-N,N-dimethylacetamide;
2-(7-chloro-9-methyl-2-pyridin-3-yl-9H-pyrimido[4,5-b]indol-4-yl)-N,N-dimethylacetamide;
N,N-dimethyl-2-phenyl-9H-pyrimido[4,5-b]indole-4-carboxamide;
ethyl 7-chloro-9-methyl-2-phenyl-9H-pyrimido[4,5-b]indole-4-carboxylate;
methyl 7-chloro-9-methyl-2-phenyl-9H-pyrimido[4,5-b]indole-4-carboxylate;
7-chloro-9-methyl-2-phenyl-9H-pyrimido[4,5-b]indole-4-carboxylic acid;
7-chloro-N,N-9-trimethyl-2-(6-methylpyridin-3-yl)-9H-pyrimido[4,5-b]indole-4-carboxamide;
7-chloro-2-(6-methoxypyridin-3-yl)-N,N,9-trimethyl-9H-pyrimido[4,5-b]indole-4-carboxamide;
7-chloro-N,N-9-trimethyl-2-(2-methylpyridin-4-yl)-9H-pyrimido[4,5-b]indole-4-carboxamide;
7-chloro-2-(2-methoxypyridin-4-yl)-N,N,9-trimethyl-9H-pyrimido[4,5-b]indole-4-carboxamide;
7-chloro-9-isobutyl-N,N-dimethyl-2-pyridin-4-yl-9H-pyrimido[4,5-b]indole-4-carboxamide;
7-chloro-2-cyclopropyl-N,N,9-trimethyl-9H-pyrimido[4,5-b]indole-4-carboxamide;
7-chloro-N,N,2,9-tetramethyl-9H-pyrimido[4,5-b]indole-4-carboxamide;
7-chloro-2-isopropyl-N,N,9-trimethyl-9H-pyrimido[4,5-b]indole-4-carboxamide;
7-chloro-N,N,9-trimethyl-2-(tetrahydro-2H-pyran-4-yl)-9H-pyrimido[4,5-b]indole-4-carboxamide;
7-chloro-2-{4-[(dimethylamino)methyl]phenyl}-N,N,9-trimethyl-9H-pyrimido[4,5-b]indole-4-carboxamide;
7-chloro-2-(6-chloropyridin-3-yl)-N,N,9-trimethyl-9H-pyrimido[4,5-b]indole-4-carboxamide;
7-chloro-N,N,9-trimethyl-2-[6-(trifluoromethyl)pyridin-3-yl]-9H-pyrimido[4,5-b]indole-4-carboxamide;
7-chloro-2-(6-ethoxypyridin-3-yl)-N,N,9-trimethyl-9H-pyrimido[4,5-b]indole-4-carboxamide;
7-chloro-2-(6-ethylpyridin-3-yl)-N,N,9-trimethyl-9H-pyrimido[4,5-b]indole-4-carboxamide;
7-chloro-2-(5-ethylpyridin-3-yl)-N,N,9-trimethyl-9H-pyrimido[4,5-b]indole-4-carboxamide;
7-chloro-N,N,9-trimethyl-2-(5-methylpyridin-3-yl)-9H-pyrimido[4,5-b]indole-4-carboxamide;
7-chloro-N,N,9-trimethyl-2-pyrimidin-5-yl-9H-pyrimido[4,5-b]indole-4-carboxamide;
7-chloro-2-(5-methoxypyridin-3-yl)-N,N,9-trimethyl-9H-pyrimido[4,5-b]indole-4-carboxamide;
7-chloro-2-[6-(methoxymethyl)pyridin-3-yl]-N,N,9-trimethyl-9H-pyrimido[4,5-b]indole-4-carboxamide;
7-chloro-N,N,9-trimethyl-2-(2-methyl-1,3-thiazol-4-yl)-9H-pyrimido[4,5-b]indole-4-carboxamide;
7-chloro-2-{6-[(dimethylamino)methyl]pyridin-3-yl}-N,N,9-trimethyl-9H-pyrimido[4,5-b]indole-4-carboxamide;
7-chloro-2-(5,6-dimethylpyridin-3-yl)-N,N,9-trimethyl-9H-pyrimido[4,5-b]indole-4-carboxamide;
7-chloro-N,N,9-trimethyl-2-(5,6,7,8-tetrahydroquinolin-3-yl)9H-pyrimido[4,5-b]indole-4-carboxamide; and
7-chloro-2-(2,6-dimethylpyridin-4-yl)-N,N,9-trimethyl-9H-pyrimido[4,5-b]indole-4-carboxamide; or
a salt of said compound or a hydrate or a solvate of said compound or said salt.

5. A process for preparing a compound of formula (I) according to claim 1 comprising the step of:
cyclizing the compound of formula (III):

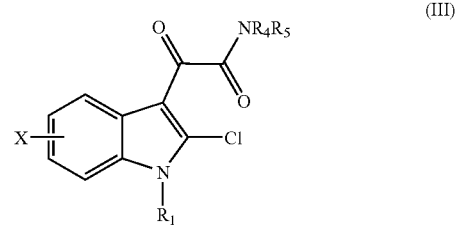

(III)

in which X, $R_1$, $R_4$ and $R_5$ are as defined in claim 1,
in the presence of an alkyl, heteroalkyl, aryl or heteroaryl amidine of general formula $R_2C(NH)NH_2$ in which $R_2$ is as defined in claim 1, by heating in an apolar or polar solvent selected from xylene or N,N-dimethylformamide in order to result in a compound of general formula (I) in which n is equal to 0 and Y represents an $NR_4R_5$ group.

6. A process for preparing a compound of formula (I) according to claim 1 comprising the step of:
carbonylating the compound of formula (VII):

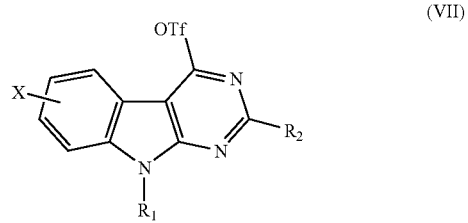

(VII)

in which X, $R_1$ and $R_2$ are as defined in claim 1 and OTf represents a triflate group,
in the presence of palladium acetate, 1,3-bis(diphenylphosphino)propane and an alcohol of formula $R_3OH$, in which $R_3$ is as defined in claim 1, in order to obtain the compound of formula (I) in which n is equal to 0 and Y represents an $OR_3$ group.

7. A process for preparing a compound of formula (I) according to claim 1, comprising the step of:
saponifying and decarboxylating the compound of formula (IX):

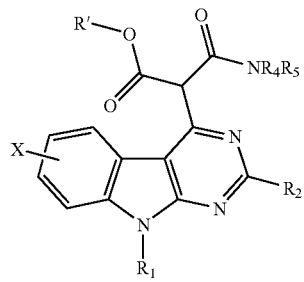

in which X, $R_1$, $R_2$, $R_4$ and $R_5$ are as defined in claim 1 and R' represents a $(C_1-C_6)$alkyl,
in the presence of lithium hydroxide and a mixture of methanol, water and an ethereal solvent, in order to obtain the compound of formula (I) in which n is equal to 1 and Y represents an $NR_4R_5$ group.

8. A compound of formula (VII):

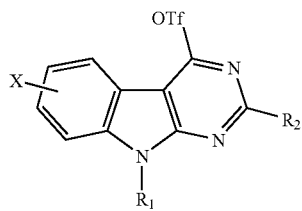

in which
OTf represents a triflate group;
X represents a hydrogen or halogen atom;
$R_1$ represents a hydrogen atom or a $(C_1-C_6)$alkyl group; and
$R_2$ represents a $(C_1-C_6)$alkyl group, a phenyl or a monocyclic or bicyclic heterocycle, said phenyl or heterocycle groups optionally bearing one or more halogen atoms and/or one or more $(C_1-C_6)$alkyl, $(C_1-C_6)$alkoxyl, $(C_1-C_6)$alkoxy$(C_1-C_6)$alkyl, $(C_1-C_6)$alkylamino $(C_1-C_6)$alkyl or $(C_1-C_6)$dialkylamino $(C_1-C_6)$alkyl groups.

9. A compound of formula (IX):

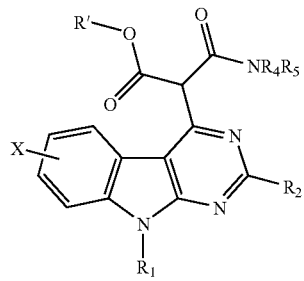

in which
X represents a hydrogen or halogen atom;
R' represents a $(C_1-C_6)$alkyl;
$R_1$ represents a hydrogen atom or a $(C_1-C_6)$alkyl group;
$R_2$ represents a $(C_1-C_6)$alkyl group, a phenyl or a monocyclic or bicyclic heterocycle, said phenyl or heterocycle groups optionally bearing one or more halogen atoms and/or one or more $(C_1-C_6)$alkyl, $(C_1-C_6)$alkoxyl, $(C_1-C_6)$alkoxy $(C_1-C_6)$alkyl, $(C_1-C_6)$alkylamino $(C_1-C_6)$alkyl or $(C_1-C_6)$dialkylamino $(C_1-C_6)$alkyl groups; and
$R_4$ and $R_5$ each represent, independently of one another, a hydrogen atom or a $(C_1-C_6)$alkyl group, or else $R_4$ and $R_5$ form, with the nitrogen atom that they bear, an aziridinyl, azetidinyl, pyrrolidinyl, piperidinyl, morpholinyl, thiomorpholinyl or piperazinyl, optionally substituted by a $(C_1-C_6)$alkyl, phenyl or heterocycle.

10. A pharmaceutical composition comprising a compound of formula (I) or a pharmaceutically acceptable salt, a hydrate or a solvate of said compound in combination with at least one pharmaceutically acceptable excipient:

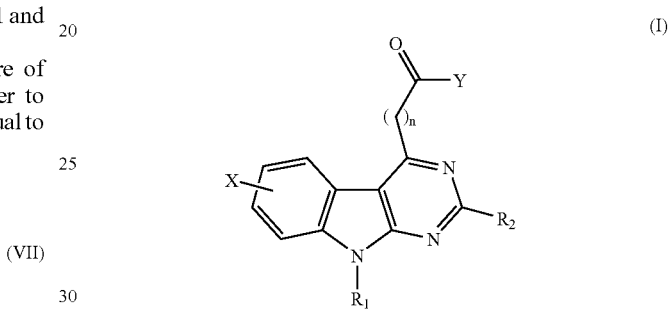

in which:
n represents the number 0 or 1;
X represents a hydrogen or halogen atom;
Y represents an $OR_3$ group or an $NR_4R_5$ group;
$R_1$ represents a hydrogen atom or a $(C_1-C_6)$alkyl group;
$R_2$ represents a $(C_1-C_6)$alkyl group, a phenyl or a monocyclic or bicyclic heterocycle, said phenyl or heterocycle groups optionally bearing one or more halogen atoms and/or one or more $(C_1-C_6)$alkyl, $(C_1-C_6)$alkoxyl, $(C_1-C_6)$alkoxy$(C_1-C_6)$alkyl, $(C_1-C_6)$alkylamino $(C_1-C_6)$alkyl or $(C_1-C_6)$dialkylamino $(C_1-C_6)$alkyl groups;
$R_3$ represents a hydrogen atom, a $(C_1-C_6)$alkyl group or a benzyl; and
$R_4$ and $R_5$ each represent, independently of one another, a hydrogen atom or a $(C_1-C_6)$alkyl group, or else $R_4$ and $R_5$ form, with the nitrogen atom that they bear, an aziridinyl, azetidinyl, pyrrolidinyl, piperidinyl, morpholinyl, thiomorpholinyl or piperazinyl, optionally substituted by a $(C_1-C_6)$alkyl, phenyl or heterocycle.

11. The composition according to claim 10, wherein:
n represents the number 0 or 1;
X represents a hydrogen or halogen atom;
Y represents an $OR_3$ group or an $NR_4R_5$ group;
$R_1$ represents a hydrogen atom or a $(C_1-C_6)$alkyl group;
$R_2$ represents a phenyl or a heterocycle chosen from pyridinyl, pyrimidinyl, pyrazinyl or pyridazinyl, the phenyl or heterocycle optionally bearing one or more halogen atoms and/or one or more $(C_1-C_6)$alkyl or $(C_1-C_6)$alkoxyl groups;
$R_3$ represents a hydrogen atom, a $(C_1-C_6)$alkyl or a benzyl; and
$R_4$ and $R_5$ each represent, independently of one another, a hydrogen atom or a $(C_1-C_6)$alkyl group, or else $R_4$ and $R_5$ form, with the nitrogen atom that they bear, an aziridinyl, azetidinyl, pyrrolidinyl, piperidinyl, morpholinyl, thiomorpholinyl or piperazinyl group, optionally substituted by a $(C_1-C_6)$alkyl, phenyl or azetidinyl.

12. The composition according to claim 10, wherein:
n represents the number 0 or 1;
X represents a hydrogen or fluorine or chlorine atom;
Y represents a hydroxy, $OCH_3$, $O(CH_2CH_3)$, $N(CH_3)_2$, $N(CH_2CH_3)_2$, pyrrolidinyl, piperidinyl, morpholinyl, (N-azetidinyl)piperidinyl or N-methylpiperazinyl group;
$R_1$ represents a hydrogen atom, a methyl or isobutyl group; and
$R_2$ represents a phenyl, a methyl, isopropyl or cyclopropyl group or a heterocycle chosen from pyridinyl, pyrazinyl, pyrimidinyl, thiazolyl, tetrahydroquinolinyl or tetrahydropyranyl, the phenyl and heterocycle groups optionally being substituted by one or more halogen groups and/or one or more $(C_1-C_6)$alkyl, $(C_1-C_6)$alkoxyl, $(C_1-C_6)$alkoxy$(C_1-C_6)$alkyl, $(C_1-C_6)$dialkylamino or $(C_1-C_6)$dialkylamino $(C_1-C_6)$alkyl groups.

13. The composition according to claim 10, wherein the compound is selected from the group consisting of:
N,N,9-trimethyl-2-phenyl-9H-pyrimido[4,5-b]indole-4-carboxamide;
7-chloro-N,N,9-trimethyl-2-phenyl-9H-pyrimido[4,5-b]indole-4-carboxamide;
7-fluoro-N,N-9-trimethyl-2-phenyl-9H-pyrimido[4,5-b]indole-4-carboxamide;
6-chloro-N,N-9-trimethyl-2-phenyl-9H-pyrimido[4,5-b]indole-4-carboxamide;
7-chloro-N,N-dimethyl-2-phenyl-9H-pyrimido[4,5-b]indole-4-carboxamide;
7-chloro-N,N-diethyl-9-methyl-2-phenyl-9H-pyrimido[4,5-b]indole-4-carboxamide;
7-chloro-9-methyl-2-phenyl-4-(pyrrolidin-1-ylcarbonyl)-9H-pyrimido[4,5-b]indole;
7-chloro-9-methyl-2-phenyl-4-(piperidin-1-ylcarbonyl)-9H-pyrimido[4,5-b]indole;
7-chloro-9-methyl-4-(morpholin-4-ylcarbonyl)-2-phenyl-9H-pyrimido[4,5-b]indole;
4-[(4-azetidin-1-yl)piperidin-1-ylcarbonyl]-7-chloro-9-methyl-2-phenyl-9H-pyrimido-[4,5-b]indole;
7-chloro-9-methyl-4-[(4-methylpiperazin-1-yl)carbonyl]-2-phenyl-9H-pyrimido[4,5-b]indole;
6-chloro-N,N-9-trimethyl-2-pyridin-4-yl-9H-pyrimido[4,5-b]indole-4-carboxamide;
7-fluoro-N,N,9-trimethyl-2-pyridin-4-yl-9H-pyrimido[4,5-b]indole-4-carboxamide;
7-chloro-9-methyl-2-pyridin-4-yl-4-(pyrrolidin-1-ylcarbonyl)-9H-pyrimido-[4,5-b]indole;
7-chloro-N,N,9-trimethyl-2-pyridin-4-yl-9H-pyrimido[4,5-b]indole-4-carboxamide;
7-chloro-N,N,9-trimethyl-2-pyridin-3-yl-9H-pyrimido[4,5-b]indole-4-carboxamide;
7-chloro-N,N-9-trimethyl-2-pyridin-2-yl-9H-pyrimido[4,5-b]indole-4-carboxamide
7-chloro-N,N-9-trimethyl-2-pyrazin-2-yl-9H-pyrimido[4,5-b]indole-4-carboxamide;
2-(7-chloro-9-methyl-2-phenyl-9H-pyrimido[4,5-b]indol-4-yl)-N,N-dimethylacetamide;
2-(6-chloro-9-methyl-2-phenyl-9H-pyrimido]4,5-b]indol-4-yl)-N,N-dimethylacetamide;
2-(7-chloro-9-methyl-2-pyridin-4-yl-9H-pyrimido[4,5-b]indol-4-yl)-N,N-dimethylacetamide;
2-(7-chloro-9-methyl-2-pyridin-3-yl-9H-pyrimido[4,5-b]indol-4-yl)-N,N-dimethylacetamide;
N,N-dimethyl-2-phenyl-9H-pyrimido[4,5-b]indole-4-carboxamide;
ethyl 7-chloro-9-methyl-2-phenyl-9H-pyrimido[4,5-b]indole-4-carboxylate;
methyl 7-chloro-9-methyl-2-phenyl-9H-pyrimido[4,5-b]indole-4-carboxylate;
7-chloro-9-methyl-2-phenyl-9H-pyrimido[4,5-b]indole-4-carboxylic acid;
7-chloro-N,N-9-trimethyl-2-(6-methylpyridin-3-yl)-9H-pyrimido[4,5-b]indole-4-carboxamide;
7-chloro-2-(6-methoxypyridin-3-yl)-N,N,9-trimethyl-9H-pyrimido[4,5-b]indole-4-carboxamide;
7-chloro-N,N-9-trimethyl-2-(2-methylpyridin-4-yl)-9H-pyrimido[4,5-b]indole-4-carboxamide;
7-chloro-2-(2-methoxypyridin-4-yl)-N,N,9-trimethyl-9H-pyrimido[4,5-b]indole-4-carboxamide;
7-chloro-9-isobutyl-N,N-dimethyl-2-pyridin-4-yl-9H-pyrimido[4,5-b]indole-4-carboxamide;
7-chloro-2-cyclopropyl-N,N,9-trimethyl-9H-pyrimido[4,5-b]indole-4-carboxamide;
7-chloro-N,N,2,9-tetramethyl-9H-pyrimido[4,5-b]indole-4-carboxamide;
7-chloro-2-isopropyl-N,N,9-trimethyl-9H-pyrimido[4,5-b]indole-4-carboxamide;
7-chloro-N,N,9-trimethyl-2-(tetrahydro-2H-pyran-4-yl)-9H-pyrimido[4,5-b]indole-4-carboxamide;
7-chloro-2-{4-[(dimethylamino)methyl]phenyl}-N,N,9-trimethyl-9H-pyrimido[4,5-b]indole-4-carboxamide;
7-chloro-2-(6-chloropyridin-3-yl)-N,N,9-trimethyl-9H-pyrimido[4,5-b]indole-4-carboxamide;
7-chloro-N,N,9-trimethyl-2-[6-(trifluoromethyl)pyridin-3-yl]-9H-pyrimido[4,5-b]indole-4-carboxamide;
7-chloro-2-(6-ethoxypyridin-3-yl)-N,N,9-trimethyl-9H-pyrimido[4,5-b]indole-4-carboxamide;
7-chloro-2-(6-ethylpyridin-3-yl)-N,N,9-trimethyl-9H-pyrimido[4,5-b]indole-4-carboxamide;
7-chloro-2-(5-ethylpyridin-3-yl)-N,N,9-trimethyl-9H-pyrimido[4,5-b]indole-4-carboxamide;
7-chloro-N,N,9-trimethyl-2-(5-methylpyridin-3-yl)-9H-pyrimido[4,5-b]indole-4-carboxamide;
7-chloro-N,N,9-trimethyl-2-pyrimidin-5-yl-9H-pyrimido[4,5-b]indole-4-carboxamide;
7-chloro-2-(5-methoxypyridin-3-yl)-N,N,9-trimethyl-9H-pyrimido[4,5-b]indole-4-carboxamide;
7-chloro-2-[6-(methoxymethyl)pyridin-3-yl]-N,N,9-trimethyl-9H-pyrimido[4,5-b]indole-4-carboxamide;
7-chloro-N,N,9-trimethyl-2-(2-methyl-1,3-thiazol-4-yl)-9H-pyrimido[4,5-b]indole-4-carboxamide;
7-chloro-2-{6-[(dimethylamino)methyl]pyridin-3-yl}-N,N,9-trimethyl-9H-pyrimido[4,5-b]indole-4-carboxamide;
7-chloro-2-(5,6-dimethylpyridin-3-yl)-N,N,9-trimethyl-9H-pyrimido[4,5-b]indole-4-carboxamide;
7-chloro-N,N,9-trimethyl-2-(5,6,7,8-tetrahydroquinolin-3-yl)9H-pyrimido[4,5-b]indole-4-carboxamide; and
7-chloro-2-(2,6-dimethylpyridin-4-yl)-N,N,9-trimethyl-9H-pyrimido[4,5-b]indole-4-carboxamide;
or a pharmaceutically acceptable salt thereof.

* * * * *

UNITED STATES PATENT AND TRADEMARK OFFICE
CERTIFICATE OF CORRECTION

PATENT NO. : 7,547,706 B2  Page 1 of 1
APPLICATION NO. : 11/873789
DATED : June 16, 2009
INVENTOR(S) : Jacques Froissant et al.

It is certified that error appears in the above-identified patent and that said Letters Patent is hereby corrected as shown below:

In the Specification:
In column 29, line 35 (Excluding Structure), delete "NCCH$_3$)$_2$" and insert -- N(CH$_3$)$_2$ --, therefor.

Signed and Sealed this

Twenty-ninth Day of June, 2010

David J. Kappos
*Director of the United States Patent and Trademark Office*